(12) United States Patent
Lu

(10) Patent No.: US 12,743,164 B2
(45) Date of Patent: Sep. 22, 2026

(54) OBTAINING WELLNESS INSIGHTS USING AN INPUT DEVICE

(71) Applicant: Apple Inc., Cupertino, CA (US)

(72) Inventor: Hsiang-Chun Lu, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/787,641

(22) Filed: Jul. 29, 2024

(65) Prior Publication Data

US 2025/0044883 A1 Feb. 6, 2025

Related U.S. Application Data

(60) Provisional application No. 63/517,838, filed on Aug. 4, 2023.

(51) Int. Cl.
*G06F 3/0354* (2013.01)
*G16H 50/30* (2018.01)
*H04L 67/306* (2022.01)

(52) U.S. Cl.
CPC ......... *G06F 3/03545* (2013.01); *G16H 50/30* (2018.01); *H04L 67/306* (2013.01)

(58) Field of Classification Search
CPC .... G06F 3/03545; G16H 50/30; H04L 67/306
See application file for complete search history.

(56) References Cited

U.S. PATENT DOCUMENTS 9,994,296 B1 * 6/2018 Balogh .................. B63B 79/10
2013/0013327 A1 1/2013 Horseman
2013/0147809 A1 * 6/2013 Luo .......................... G09G 5/28 345/472.3
2013/0338539 A1 12/2013 Bailey et al.
2016/0013571 A1 1/2016 Ning
2019/0076078 A1 3/2019 Davis et al.
2021/0272698 A1 * 9/2021 Nakajima .............. G16H 20/30
2022/0415205 A1 * 12/2022 Won ................... G06V 30/1801
2023/0136754 A1 * 5/2023 Asis ....................... G16H 40/63 705/2
2025/0251817 A1 * 8/2025 Chen ..................... G06F 3/0383

FOREIGN PATENT DOCUMENTS

CN 115246281 A 10/2022
CN 116052888 A 5/2023
WO 2017/217597 A1 12/2017

* cited by examiner

*Primary Examiner* — Robert J Michaud
(74) *Attorney, Agent, or Firm* — Kubota & Basol LLP

(57) ABSTRACT

A system including a stylus with an inertial measurement unit (IMU) and force/touch/temperature sensors on its sides and/or tip, in some instances in conjunction with force/touch sensors on a tablet computing device or sensors on a watch, is disclosed that obtains measurements such as stylus grip pressure, tilt and touch location, stylus tip pressure, stylus motion, and user temperature. In some instances, these measurements can be obtained through everyday use of the stylus, while in other instances, the user can be prompted to perform certain tasks (e.g., draw specific contours) to assist in data collection. With these measurements, a user profile and baseline profile data can be established and tracked over time, which can include parameters such as tremor amplitude and grip strength. Deviations from baseline profile data can be computed, and when those deviations exceed a threshold, an alert or other wellness insights can be presented to the user.

18 Claims, 7 Drawing Sheets

114
Mobile
Telephone
100
Touch
Screen
102

Touch
Screen
102
114
Media
Player
104

Touch
Screen
102
Personal
Computer
106
114
114
Track Pad
108

Touch
Screen
102
Tablet
Computer
110
114

Wearable
Device
112
114
Touch
Screen
102

OBTAINING WELLNESS INSIGHTS USING AN INPUT DEVICE

CROSS-REFERENCE TO RELATED APPLICATIONS

This application claims the benefit of U.S. Provisional Application No. 63/517,838, filed Aug. 4, 2023, the content of which is herein incorporated by reference in its entirety for all purposes.

FIELD OF THE DISCLOSURE

This relates generally to evaluating a person's wellness state, and more particularly to providing wellness insights for a user of an input device such as a stylus.

BACKGROUND OF THE DISCLOSURE

A person's state of wellness can be hard to evaluate, especially when symptoms of decline or improvement occur gradually. Specific tests such as those prescribed by a health care provider are often administered infrequently or on a one-time, as-needed basis, and thus may be unable to detect a gradual decline or improvement in a person's wellness state. Moreover, because such tests are often performed with the person's full awareness, they can be subject to unintended and imperceptible changes in the person's behavior, which can lead to inaccurate results.

SUMMARY OF THE DISCLOSURE

Styluses have become popular input devices for touch-sensitive devices. Touching or hovering a stylus over a touch-sensitive device at a location often dictated by a user interface (UI) being displayed by the touch-sensitive device can allow a user to perform various functions. In general, the touch-sensitive device can recognize a stylus touch or hover event and the position of the event on the touch panel, and the computing system can then interpret the event in accordance with the display appearing at the time of the event, and thereafter can perform one or more actions based on the event. Because styluses have become more commonplace as handheld input devices for everyday use and for relatively long stretches of time, they can be good candidates to assist in capturing wellness-related data and providing wellness insights to a user.

Some examples of the disclosure are directed to a stylus that includes one or more inertial measurement units (IMUs), gyroscopes, accelerometers, and/or force/touch/temperature sensors on its sides and/or tip, in some instances in conjunction with force/touch sensors on a tablet computing device or sensors on a watch, to obtain measurements such as stylus grip pressure, tilt and touch location, stylus tip pressure, stylus motion, and user temperature. In some instances, these measurements can be obtained through everyday use of the stylus, while in other instances, the user can be prompted to perform certain tasks (e.g., draw specific contours, shapes or letters) to assist in data collection. With these measurements, a user profile and baseline profile data can be established and tracked over time, which can include wellness parameters such as tremor amplitude and grip strength. Deviations from baseline profile data can be computed and monitored, and when those deviations exceed a certain threshold, an alert or other wellness insights can be presented to the user.

DETAILED DESCRIPTION

In the following description of examples, reference is made to the accompanying drawings which form a part hereof, and in which it is shown by way of illustration specific examples that can be practiced. It is to be understood that other examples can be used, and structural changes can be made without departing from the scope of the disclosed examples.

Some examples of the disclosure are directed to a stylus that includes one or more inertial measurement units (IMUs), gyroscopes, accelerometers, and/or force/touch/temperature sensors on its sides and/or tip, in some instances in conjunction with force/touch sensors on a tablet computing device or sensors on a watch, to obtain measurements such as stylus grip pressure, tilt and touch location, stylus tip pressure, stylus motion, and user temperature. In some instances, these measurements can be obtained through everyday use of the stylus, while in other instances, the user can be prompted to perform certain tasks (e.g., draw specific contours, shapes or letters) to assist in data collection. With these measurements, a user profile and baseline profile data can be established and tracked over time, which can include wellness parameters such as tremor amplitude and grip strength. Deviations from baseline profile data can be computed and monitored, and when those deviations exceed a certain threshold, an alert or other wellness insights can be presented to the user.

Figures 1A, 1B, 1C, 1D, 1E:
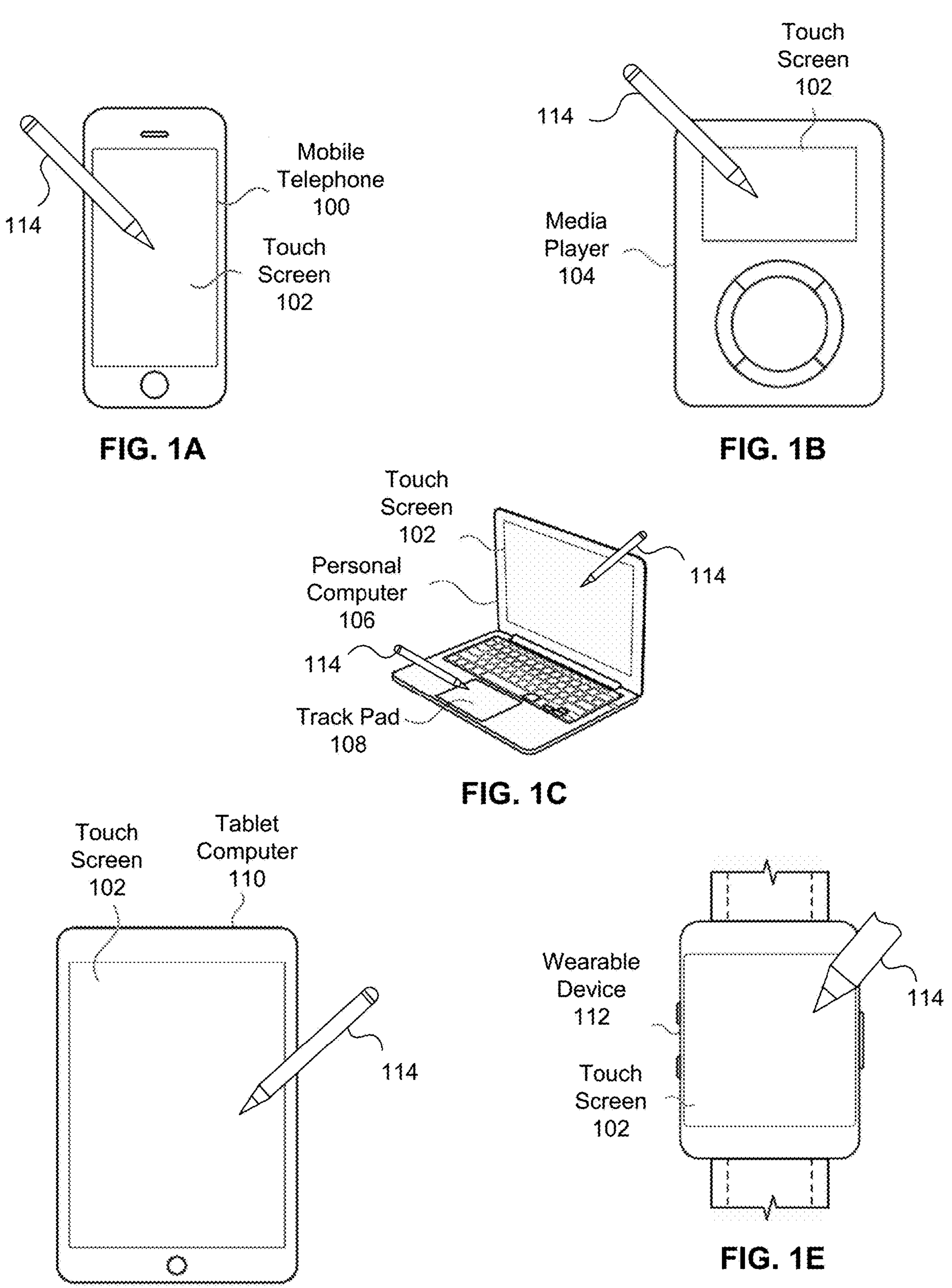
FIGS. 1A-1E illustrate examples of systems including an input device such as a stylus and a device with a touch screen or touch-sensitive surface that can accept input from the input device, wherein the system can provide wellness insights to a user based on data obtained through user contact with the input device according to some examples of the disclosure.

FIGS. 1A-1E illustrate examples of systems including an input device such as a stylus and a device with a touch screen or touch-sensitive surface that can accept input from the input device, wherein the system can provide wellness insights to a user based on data obtained through user contact with the input device according to some examples of the disclosure. FIG. 1A illustrates example mobile telephone 100 that includes touch screen 102 that can accept input from input device 114, such as a stylus, and can provide wellness insights to a user from data obtained through user contact with the input device according to some examples of the disclosure. FIG. 1B illustrates example digital media player 104 that includes touch screen 102 that can accept input from input device 114, such as a stylus, and can provide wellness insights to a user from data obtained through user contact with the input device according to some examples of the disclosure. FIG. 1C illustrates example personal computer 106 that includes touch screen 102 and track pad 108 that can accept input from input device 114, such as a stylus, and can provide wellness insights to a user from data obtained through user contact with the input device according to some examples of the disclosure. FIG. 1D illustrates example tablet computing device 110 that includes touch screen 102 that can accept input from input device 114, such as a stylus, and can provide wellness insights to a user from data obtained through user contact with the input device according to some examples of the disclosure. FIG. 1E illustrates example wearable device 112 (e.g., a watch) that includes touch screen 102 that can accept input from input device 114, such as a stylus, and can provide wellness insights to a user from data obtained through user contact with the input device according to some examples of the disclosure. Note that although the devices illustrated in FIGS. 1A-1E include touch screens, in some examples, the devices may have a non-touch sensitive display. In other examples, input devices such as a stylus may be used in conjunction with devices that do not employ a touch screen or touch-sensitive surface, such as a head-mounted display that presents a 3D environment to a user.

It should be understood that the devices illustrated in the systems of FIGS. 1A-1E are provided only as nonlimiting examples. Other devices that can accept input from input device 114 and provide wellness insights to a user from data obtained through user contact with the input device are contemplated according to various examples of the disclosure. Furthermore, although input devices 114 of FIGS. 1A-1E are illustrated as styluses, other handheld or wearable input devices capable of receiving sustained user contact, such as earbuds, headphones, head-mounted devices, smart glasses, headbands, watches, computer mice, remote controls, chest straps, wrist straps, rings, etc. also fall within the scope of this disclosure.

In some examples, touch screen 102 can be based on self-capacitance. A self-capacitance based touch system can include a matrix of small, individual plates of conductive material or groups of individual plates of conductive material forming larger conductive regions that can be referred to as touch electrodes or as touch node electrodes. For example, a touch screen can include a plurality of individual touch electrodes, each touch electrode identifying or representing a unique location (e.g., a touch node) on the touch screen at which touch or proximity is to be sensed, and each touch node electrode being electrically isolated from the other touch node electrodes in the touch screen/panel. Such a touch screen can be referred to as a pixelated self-capacitance touch screen, though it is understood that in some examples, the touch node electrodes on the touch screen can be used to perform scans other than self-capacitance scans on the touch screen (e.g., mutual capacitance scans). During operation, a touch node electrode can be stimulated with an alternating current (AC) waveform, and the self-capacitance to ground of the touch node electrode can be measured. As an object approaches the touch node electrode, the self-capacitance to ground of the touch node electrode can change (e.g., increase). This change in the self-capacitance of the touch node electrode can be detected and measured by the touch sensing system to determine the positions of multiple objects when they touch, or come in proximity to, the touch screen. In some examples, the touch node electrodes of a self-capacitance based touch system can be formed from rows and columns of conductive material, and changes in the self-capacitance to ground of the rows and columns can be detected, similar to above. In some examples, a touch screen can be multi-touch, single touch, projection scan, full-imaging multi-touch, capacitive touch, etc.

In some examples, touch screens 102 can be based on mutual capacitance. A mutual capacitance based touch system can include electrodes arranged as drive and sense lines that may cross over each other on different layers (in a double-sided configuration) or may be adjacent to each other on the same layer. The crossing or adjacent locations can form touch nodes. During operation, the drive line can be stimulated with an AC waveform and the mutual capacitance of the touch node can be measured. As an object approaches the touch node, the mutual capacitance of the touch node can change (e.g., decrease). This change in the mutual capacitance of the touch node can be detected and measured by the touch sensing system to determine the positions of multiple objects when they touch, or come in proximity to, the touch screen. As described herein, in some examples, a mutual capacitance based touch system can form touch nodes from a matrix of small, individual plates of conductive material.

In some examples, touch screens 102 can be based on mutual capacitance and/or self-capacitance. The electrodes can be arranged as a matrix of small, individual plates of conductive material or as drive lines and sense lines, or in another pattern. The electrodes can be configurable for mutual capacitance or self-capacitance sensing or a combination of mutual and self-capacitance sensing. For example, in one mode of operation electrodes can be configured to sense mutual capacitance between electrodes and in a different mode of operation electrodes can be configured to sense self-capacitance of electrodes. In some examples, some of the electrodes can be configured to sense mutual capacitance therebetween and some of the electrodes can be configured to sense self-capacitance thereof.

Figure 2:
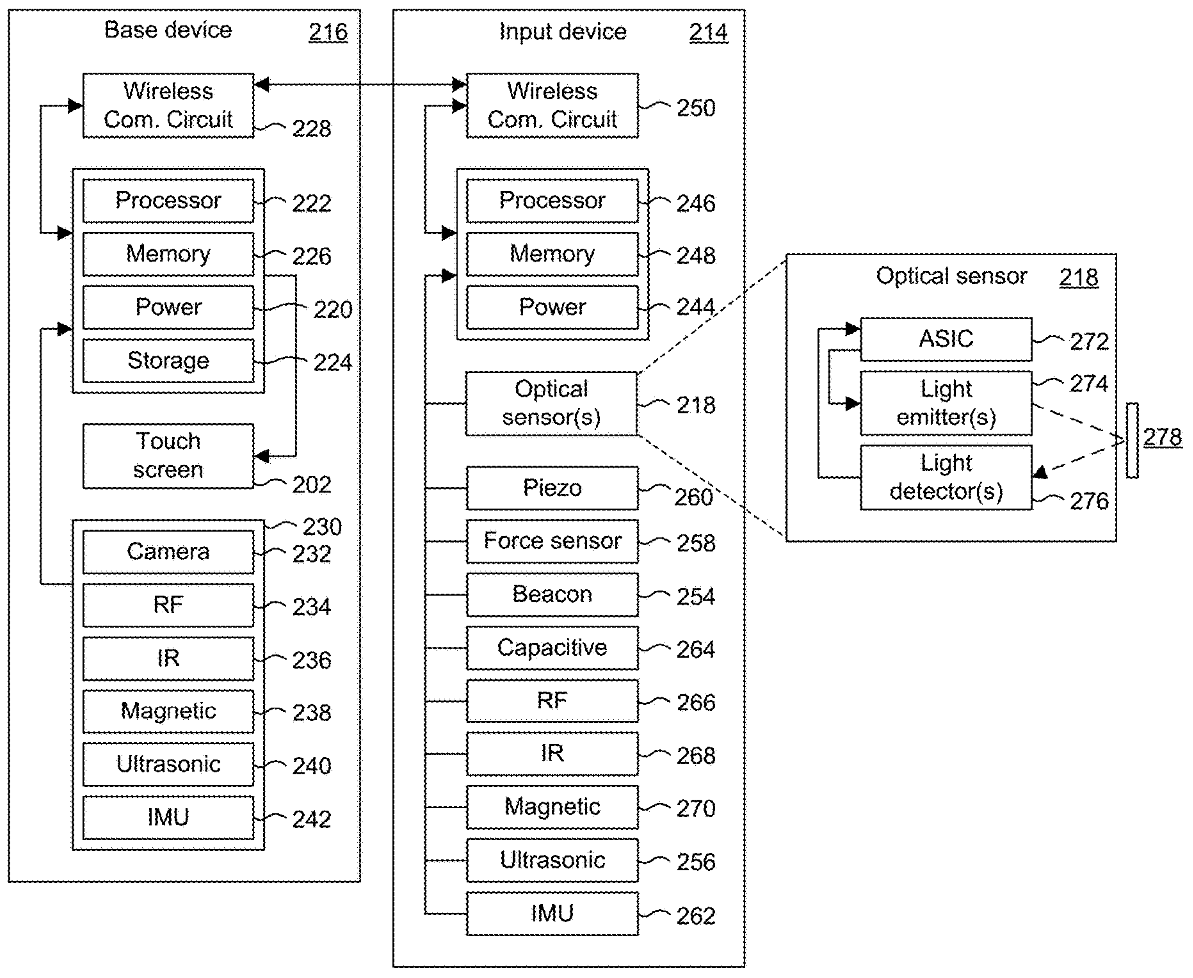
FIG. 2 illustrates a block diagram of a system including a base device and an input device for providing wellness insights to a user, wherein the input device includes an optional optical sensor according to some examples of the disclosure.

FIG. 2 illustrates a block diagram of a system including base device 216 (corresponding to one of the devices shown in FIGS. 1A-1E) and input device 214 for providing wellness insights to a user, wherein the input device includes an optional optical sensor 218 according to some examples of the disclosure. Base device 216 can receive input from input device 214 and render content for display generated using the input device, such as writing or drawing by a stylus. Additionally, base device 216 can receive input from input device 214 and maintain a profile of user data for use in determining and providing wellness insights to the user. Note that the block diagram of FIG. 2 is merely exemplary, and that some of the blocks may be optional.

In some examples, base device 216 can include touch screen 202 to display images and to detect touch and/or proximity (e.g., hover) events from an object (e.g., input device 214) at or proximate to the surface of the touch screen. In some examples, touch screen 202 can be configured to display content generated using input device 214 (e.g., content generated by writing or drawing on the touch screen with a stylus). In some examples, base device 216 can include a non-touch sensitive display configured to display content generated using input device 214 (e.g., writing or drawing on a non-touch sensitive surface with an object).

In some examples, base device 216 can include power source 220 (e.g., energy storage device such as a battery), host processor 222, program storage 224 and/or memory 226, wireless communication circuitry 228, and optional sensors 230. Host processor 222 can control some or all of the operations of base device 216. Host processor 222 can communicate, either directly or indirectly, with some or all of the other components of base device 216. For example, a system bus or other communication mechanism can provide communication between power source 220, host processor 222, touch screen 202, program storage 224, memory 226, wireless communication circuitry 228, and sensors 230.

Host processor 222 can be implemented as any electronic component capable of processing, receiving, or transmitting data or instructions, whether such data or instructions is in the form of software or firmware or otherwise encoded. For example, host processor 222 can include a microprocessor, a central processing unit (CPU), an application-specific integrated circuit (ASIC), a digital signal processor (DSP), a controller, or a combination of such component. As described herein, the term "processor" or "processing circuitry" is meant to encompass a single processor or processing unit, multiple processors, multiple processing units, or other suitably configured computing element or elements.

Host processor 222 can receive touch input from touch screen 202 or other input devices and perform actions based on the outputs. For example, host processor 222 can be connected to program storage 224 (and/or memory 226) and a display controller/driver to generate images on touch screen 202. Touch screen 202 can include, but is not limited to, Liquid Crystal Display (LCD) displays, Light-Emitting Diode (LED) displays, including Organic LED (OLED), Active-Matrix Organic LED (AMOLED), Passive-Matrix Organic LED (PMOLED) displays, a projector, a holographic projector, a retinal projector, or other suitable display. In some examples, the display driver can provide voltages on select (e.g., gate) lines to each pixel transistor and can provide data signals along data lines to these same transistors to control the pixel display image for touch screen 202.

Host processor 222 can cause an image to be displayed on touch screen 202, such as a display image of a user interface (UI) or display image of content generated using input device 214, and can use touch processor and/or touch controller to detect a touch on or near the touch screen, such as a touch input at the displayed UI. The touch input can be used by computer programs stored in program storage 224 to perform actions that can include, but are not limited to, moving an object such as a cursor or pointer, scrolling or panning, adjusting control settings, opening a file or document, viewing a menu, making a selection, executing instructions, operating a peripheral device connected to the host device, answering a telephone call, placing a telephone call, terminating a telephone call, changing the volume or audio settings, storing information related to telephone communications such as addresses, frequently dialed numbers, received calls, missed calls, logging onto a computer or a computer network, permitting authorized individuals access to restricted areas of the computer or computer network, loading a user profile associated with a user's preferred arrangement of the computer desktop, permitting access to web content, launching a particular program, encrypting or decoding a message, and/or the like. Host processor 222 can also create, maintain and analyze a user profile (e.g., a hand profile of a user) based on data received from input device 214, track deltas from baseline values in the profile, and generate alerts or provide other wellness insights to the user when the deltas exceed predetermined thresholds. Host processor 222 can also perform additional functions that may not be related to touch processing.

Note that one or more of the functions described in this disclosure can be performed by firmware stored in memory 226 and/or stored in program storage 224 and executed by host processor 222 or other processing circuitry of base device 216. The firmware can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "non-transitory computer-readable storage medium" can be any medium (excluding signals) that can contain or store the program for use by or in connection with the instruction execution system, apparatus, or device. In some examples, program storage 224 and/or memory 226 can be a non-transitory computer readable storage medium. The non-transitory computer readable storage medium (or multiple thereof) can have stored therein instructions, which when executed by host processor 222 or other processing circuitry, can cause base device 216 to perform one or more functions and methods of one or more examples of this disclosure. The computer-readable storage medium can include, but is not limited to, an electronic, magnetic, optical, electromagnetic, infrared, or semiconductor system, apparatus or device, a portable computer diskette (magnetic), a random access memory (RAM) (magnetic), a read-only memory (ROM) (magnetic), an erasable programmable read-only memory (EPROM) (magnetic), a portable optical disc such a CD, CD-R, CD-RW, DVD, DVD-R, or DVD-RW, or flash memory such as compact flash cards, secured digital cards, universal serial bus (USB) memory devices, memory sticks, and the like.

The firmware can also be propagated within any transport medium for use by or in connection with an instruction execution system, apparatus, or device, such as a computer-based system, processor-containing system, or other system that can fetch the instructions from the instruction execution system, apparatus, or device and execute the instructions. In the context of this document, a "transport medium" can be any medium that can communicate, propagate or transport the program for use by or in connection with the instruction execution system, apparatus, or device. The transport medium can include, but is not limited to, an electronic, magnetic, optical, electromagnetic or infrared wired or wireless propagation medium.

Power source 220 can be implemented as any component capable of providing energy to base device 216. For example, power source 220 can include one or more batteries or rechargeable batteries. Additionally or alternatively, power source 220 can include a power connector or power cord that connects base device 216 to another power source, such as a wall outlet.

Memory 226 can store electronic data that can be used by base device 216. For example, memory 226 can store electrical data or content such as, for example, force sensing data, touch data, temperature data, acceleration data, velocity data, audio and video files, documents and applications, device settings and user preferences, timing signals, control signals, and data structures or databases. Memory 226 can include any type of memory. By way of example only, memory 226 can include random access memory, read-only memory, Flash memory, removable memory, other types of storage elements, or combinations of such memory types.

Sensors 230 can optionally include circuitry configured to sense one or more types of parameters, such as but not limited to, vibration; light; touch; force; temperature; movement; relative motion; biometric data (e.g., biological parameters) of a user; air quality; proximity; position; connectedness; and so on. In some examples, sensors 230 can include an image sensor such as outward facing camera 232, radiofrequency sensor (and/or transmitter) 234, infrared sensor (and/or transmitter) 236, magnetic sensor (and/or generator) 238 (e.g., a magnetometer), ultrasonic sensor (and/or transmitter) 240, and/or inertial measurement unit (IMU) 242. In some examples, sensors 230 can further include other sensor(s) including a force sensor, a temperature sensor, a position sensor, a light or optical sensor, an accelerometer, a pressure transducer, a gyroscope, an acoustic sensor, a health monitoring sensor, and/or an air quality sensor, among other possibilities. Additionally, sensors 230 can utilize any suitable sensing technology, including, but not limited to, interferometric, magnetic, capacitive, ultrasonic, resistive, optical, acoustic, piezoelectric, or thermal technologies.

Wireless communication circuitry 228 can transmit or receive data from another electronic device, such as from input device 214. Although wireless communication circuitry 228 is illustrated and described, it is understood that other wired communication interfaces may be used. In some examples, the wireless and/or wired communications interfaces can include, but are not limited to, cellular, Bluetooth, and/or Wi-Fi communications interfaces. Although not shown, base device 216 can also include other input/output mechanisms including one or more touch sensing input surfaces, a crown, one or more physical buttons, one or more microphones or speakers, one or more ports such as a microphone port, and/or a keyboard.

In some examples, input device 214 can be a handheld device that includes a housing. In examples where input device 214 is a stylus, the housing can include a cylindrical body (referred to herein as a stylus body) with a tip portion (referred to herein a stylus tip or tip portion) at the distal end. In some examples, the tip portion can be part of a unibody housing and in some examples, the tip portion can be removable from the cylindrical body. The housing can include an ergonomic depression (or multiple ergonomic depressions) as a guide for placement of one of a user's fingers (e.g., thumb or index finger). The ergonomic depression can result in the orientation of input device 214 in a range of positions with respect to a user's hand and finger gestures. The circuitry of input device 214 can be disposed in the housing. For example, the circuitry can include power source 244 (e.g., battery), processing circuitry (e.g., processor 246), memory 248, wireless communication circuitry 250, and various sensors. Note that one or more of the functions described in this disclosure can be performed by firmware stored in memory 248 and executed by processor 246 or other processing circuitry of input device 214. The sensors can optionally include optical sensors 218 among other possible sensors. In some examples, input device 214 can include optional beacon transmitter 254 (e.g., using any electromagnetic signals), optional ultrasonic sensor (and/or transmitter) 256, one or more touch or force sensors 258 (e.g., such as capacitive touch sensors, ultrasonic touch sensors, a strain gauge, capacitive gap force sensor, or piezoelectric sensor 260), IMU 262 (and/or other motion or orientation component such as an accelerometer or gyroscope), a capacitive electrode or other capacitive sensor 264, optional radiofrequency sensor (and/or transmitter) 266, optional infrared sensor (and/or transmitter) 268, optional magnetic sensor (and/or generator) 270, among other suitable sensors. Processor 246 can communicate, either directly or indirectly, with some or all of the other components of input device 214. For example, a system bus or other communication mechanism can provide communication between the various components of input device 214.

As described herein, in some examples, motion and/or position of input device 214 can be tracked to generate input for base device 216. In some examples, position and/or motion of input device 214 can optionally be tracked using one or more optical sensors 218. For example, input device 214 can include a single optical sensor 218 or a plurality of optical sensors. In some examples, input device 214 can be a stylus, and optical sensor(s) 218 can be disposed in the distal end of the stylus, such as in proximity the stylus tip. Optical sensor(s) 218 can be configured to both transmit and receive light (e.g., emitting and receiving a laser beam), which can provide data about the position and movement of the stylus tip relative to a non-touch-sensitive surface.

In some examples, tracking the position and/or motion of input device 214 using optical sensor(s) 218 can be augmented with additional sensors. For example, sensors 230 of base device 216 and/or the various sensors of input device 214 can track information about the input device (e.g., position, motion, orientation, force, etc. of the input device) and the information can be transferred from the one or more sensors 230 to host processor 222. The information from input device 214 (e.g., received via wireless communication circuitry 228, 250) and the one or more sensors 230 can be stored in memory 226, in some examples. The information can be processed by host processor 222 to render and/or display content on touch screen 202 from input device 214 (e.g., rendering writing or drawing by a stylus input device on non-touch sensitive surfaces on the display).

In some examples, the information about input device 214 can be gathered by, transferred to, processed by and/or stored on the input device. For example, one or more sensing modalities within input device 214 can provide additional information about input device force, orientation, motion, and/or position. The combined information from the optional optical sensors 218 and the one or more sensing modalities can then be transferred to, processed by, and/or stored on base device 216 to render and/or display content on touch screen 202, maintain a user profile, and generate alerts and other wellness insights for the user according to some examples of the disclosure. In some examples, a computing device can render content in three-dimensional environment based on position and/or motion of an input device. For example, base device 216 can be a head-mounted augmented and/or virtual reality headset that can render and overlay content over a real-world environment or a representation of a real-world environment captured by outward facing cameras 232.

Each optical sensor 218 can optionally include an application-specific integrated circuit (ASIC) 272, light emitter(s) 274, and/or one or more light detector(s) 276. As mentioned, light emitter(s) 274 can emit light onto surface 278, which in some examples can be a user's hand or other body part, and light detector(s) 276 can capture an image of an environment to detect light reflected from the surface in response to light emitted from input device 214. In some examples, light emitter(s) 274 can include a light-emitting diode (LED) or a vertical-cavity surface-emitting laser (VCSEL). In some examples, light detector(s) 276 can include an image sensor. Further, optical sensor 218 optionally includes a lens or a lens array.

It should be apparent that the architecture shown in FIG. 2 is only one example architecture of base device 216, input device 214, and optical sensor 218 and that the system could have more or fewer components than shown, or a different configuration of components. The various components shown in FIG. 2 can be implemented in hardware, software, firmware, or any combination thereof, including one or more signal processing and/or application specific integrated circuits.

Figure 3:
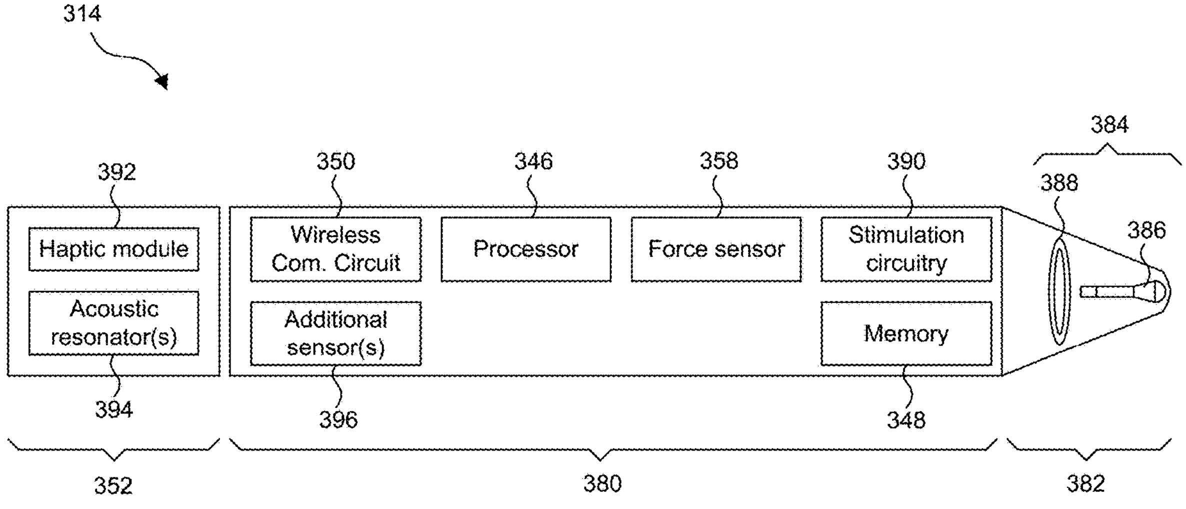
FIG. 3 illustrates a block diagram of an input device in the form of a stylus for providing wellness insights to a user according to some examples of the disclosure.

FIG. 3 illustrates a block diagram of input device 314 in the form of a stylus for providing wellness insights to a user according to some examples of the disclosure. The block diagram of FIG. 3 is a simplified version of the block diagram of input device 214 of FIG. 2. Note that the block diagram of FIG. 3 is merely exemplary, and that some of the blocks may be optional. In the example of FIG. 3, input device 314 can include optional end/cap portion 352, shaft portion 380, and tip portion 382. It should generally be understood that tip portion 382 corresponds to a first end of input device 314, and end/cap portion 352 corresponds to a second end of the input device opposite the first end. The first and second ends of input device 314 can be referred to as first and second portions that partition the input device (e.g., ends can include proximal portions of the input device, not just the distal ends). Moreover, while the example input device 314 of FIG. 3 may be described herein as an "active" stylus that stimulates a touch-sensitive surface of an electronic device, it should be understood that optional end/cap portion 352 can be incorporated into any type of stylus (e.g., a non-active stylus that does not stimulate a touch-sensitive surface of the electronic device), any type of peripheral input device, and/or any type of other peripheral device that can communicate with the base devices of FIG. 1A-1E, or with base device 216 of FIG. 2 (e.g., a keyboard, a mouse, a watch, a drawing pad, etc.). As such, any number of the active components described in connection with shaft portion 380 can be omitted from the description of input device 314 without departing from the scope of the current disclosure. Many of the features described below in connection with components of FIG. 3 relate to a default mode of input device 314, in which the input device can be used to provide active input to a device or to the user (e.g., optionally to a touch-sensitive surface of a base device). However, certain features and components described below relate to a beacon mode of input device 314, in which the stylus generates an acoustic signal that serves as a location beacon to either a human target (e.g., a user) or an electronic detector (e.g., an electronic device with one or more audio sensors).

In embodiments where input device 314 is a stylus, the input device can include one or more electrodes 384 that can be located, for example, at a first (distal) end of the input device (e.g., the tip of the stylus). As illustrated in FIG. 3, input device 314 can include tip electrode 386 and a ring electrode 388, but fewer or more electrodes may be used. Tip electrode 386 can include a material capable of transmitting the stylus stimulation signal from stimulation circuitry 390 to the touch-sensitive device, such as a flexible conductor, a metal, a conductor wrapped by a non-conductor, a non-conductor coated with a metal, a transparent conducting material (e.g., indium tin oxide (ITO)) or a transparent non-conductive material (e.g., glass) coated with a transparent (e.g., ITO) (if the tip is also used for projection purposes) or opaque material, or the like. In some examples, the input device tip can have a diameter of 2 mm or less. In some examples, the input device tip can have a diameter between 1 mm and 2 mm. Ring electrode 388 can include a conductive material, such as a flexible conductor, a metal, a conductor wrapped by a non-conductor, a non-conductor coated with a metal, a transparent conducting material (e.g., ITO) or a transparent non-conductive material (e.g., glass) coated with a transparent or opaque material, or the like.

As noted above, input device 314 can also include stimulation circuitry 390. Stimulation circuitry 390 can be configured to generate one or more stimulation signals at the one or more electrodes 384 to stimulate a touch sensor panel of a touch-sensitive device. For example, stimulation signals can be coupled from input device 314 to touch sensing circuitry of an electronic device, and can be used to determine a location of the input device at the surface of a touch screen.

The operation of stimulation circuitry 390 can be controlled by processor 346. For example, processor 346 can be configured to communicate with stimulation circuitry 390 to control the generation of stimulation signals. In some examples, the communication between processor 346 and stimulation circuitry 390 can be accomplished via an serial peripheral interface (SPI) bus, and the stimulation circuitry can operate as an SPI slave device. In some examples, input device 314 can include more than one processor, and stimulation circuitry 390 can include one or more processors. In some examples, one or more of the input device functions described herein can be performed by firmware stored in memory or in program storage (not shown) and executed by processor 346 or a processor in stimulation circuitry 390.

In examples where input device 314 is a stylus, the input device can also include one or more force sensors 358 to detect the amount of force at the sides or tip of the stylus. For example, when the stylus tip is touching a touch screen, force sensor 358 located at the tip can measure the force at the stylus tip. In another example, when a user is gripping input device 314, one or more force sensors 358 located along the sides of the input device can measure the grip pressure of the user. The force information can be stored in input device 314 (e.g., in memory 348) and/or transmitted (via a wired connection or wirelessly) to a base device. For example, the force information can be communicated to host processor 222 or a touch controller in base device 216 as shown in FIG. 2. Force information and corresponding location information can be processed together by host processor 222 and/or the touch controller in the base device.

Processor 346 can be substantially similar to processor 222 described above in connection with FIG. 2. Similar to processor 222, processor 346 can be configured to process location requests received by wireless communication circuitry 350, and optionally can be further configured to direct optional haptic module 392 to provide an appropriate drive signal to optional acoustic resonator(s) 394, such that the resonator(s) generate an acoustic signal. As an example, processor 346 can process a location request received by wireless communication circuitry 350. In some examples, processor 346 can determine a desired/specified frequency, amplitude, and/or duration of acoustic signal from the location request. Based on the processed location request, processor 346 can generate an instruction for haptic module 392 that causes the module to generate a drive signal for acoustic resonator(s) 394. As an example, the instruction for haptic module 392 can be provided to a haptic module controller (not illustrated) that interprets the instruction and determines an appropriate signal or waveform to provide the haptic module. In some examples, the functionality of a haptic module controller is performed by processor 346. In response to receiving an instruction based on the processed location request, haptic module 392 can generate a drive signal that causes acoustic resonator(s) 394 to vibrate at the particular amplitude and frequency specified in the location request, for a particular duration specified in the location request (e.g., causes the acoustic resonator(s) to generate an acoustic signal). Prior to performing the steps described above in connection with causing acoustic resonator(s) 394 to generate an acoustic signal, processor 346 may switch the stylus from a default mode to a beacon mode.

In some examples, force sensors 358 can be coupled to processor 346. Processor 346 can process force information from force sensors 358 and, based on the force information, control stylus stimulation circuitry 390 to generate or not generate stylus stimulation signals. For example, the processor can cause stylus stimulation circuitry 390 to generate no stylus stimulation signals when no force is detected or when the force is below a threshold level. When a force (or a force at or above the threshold level) is detected (e.g., corresponding to touch-down of the stylus), the processor can cause stylus stimulation circuitry 390 to generate stylus stimulation signals and continue generating stylus stimulation signals until the detected force drops below the threshold level (or some other threshold level).

Input device 314 can also include wireless communication circuitry 350, although in some examples the wireless communication functionality can be incorporated into other components within the input device, and in other examples the input device can communicate via a wired connection. In the context of examples of the disclosure, wireless communication circuitry 350 can be substantially similar to wireless communication circuitry 228 of FIG. 2, and can serve as a component by which a communication channel between input device 314 and a base device can be established and maintained. In some examples, the base device communicates requests to input device 314 by providing wireless messages to wireless communication circuitry 350, which can optionally be stored in memory 348, thereby recording the message/request history with the base device.

Wireless communication circuitry 350 can receive a location request from the base device. The location request received at wireless communication circuitry 350 can, in some examples, specify a desired amplitude, frequency, and/or duration of an acoustic signal. By generating the acoustic signal with the desired/specified amplitude, frequency, and/or duration, input device 314 can provide information to one or more audio sensors in the base device, which can in turn enable the base device to detect the presence of the input device and/or estimate a relative distance, direction, and/or position of the input device. Wireless communication circuitry 350 can be coupled to processor 346, which can be configured to process location requests received at the wireless communication circuitry. In some examples, wireless communication circuitry 350 can also transmit an acknowledgement message to the base device, which indicates successful receipt of the location request indicates that the acoustic signal specified by the request has been generated.

Wireless communication circuitry 350 can also transmit the force information (or other information, such as motion and orientation information) from input device 314 to wireless communication circuitry 228 of the base device. Wireless communication circuitry 350 can also receive other information including, but not limited to, information about input device stimulus frequencies, scan plan information (i.e., the sequence of scans to be performed by the touch-sensitive device) and clock synchronization information. For example, the base device can transmit one or more low noise frequencies to input device 314 (in the form of a stylus), and stylus stimulation circuitry 390 can generate stimulation signals at electrodes 384 based on, or at, the one or more low noise frequencies. In some examples, stylus stimulation circuitry 390 can generate stimulation signals at two or more different frequencies (e.g., at one frequency at the ring electrode and at a second frequency at the tip electrode), though in other examples, stimulation signals are only generated by the stylus at one frequency.

In some examples, input device 314 can operate asynchronously from the base device. In an asynchronous example, input device 314 can continuously generate stimulation signals, generate stimulation signals at various intervals, or generate stimulation signals when force is detected by force sensor 358. In other examples, wireless communication can be used to synchronize input device 314 and the base device. For example, input device 314 can receive clock synchronization information and scan plans from the base device such that it can generate stimulation signals when the computing system expects such stimulation signals from the input device. For example, the clock synchronization information can provide an updated value for an input device clock (e.g., a timer, counter, etc.) or reset the input device clock so that the input device clock can be substantially the same as (or otherwise track) a system clock for the base device. Input device 314 can then use the scan plan, which can define the sequence of scan events to be performed by the base device at specific times, and use the input device clock to determine when the base device expects input device stimulation signals to be generated. When the base device is not expecting stylus stimulation signals, input device 314 can stop generating stimulation signals. Additionally, in some examples, the base device and input device 314 can synchronize their communication to regular time intervals such that both the base device and the input device can save power. For example, after input device 314 and the base device pair via a wireless communication channel, the communication between the input device and the base device can occur only at specified times (based on their respective synchronized clocks). Input device 314 and/or the base device can include one or more crystals to generate stable and accurate clock signals to improve synchronization and reduce drift between the base device and input device clocks.

When input device 314 first connects or reconnects wirelessly to the base device it can receive frequency information from the base device. A stylus spectral analysis scan can determine one or more clean frequencies for input device 314 to use and generate one or more stimulation signals. The base device and input device 314 can communicate (including, for example, performing a handshake between the two devices) and the base device can transmit the frequency information to input device 314 such that the input device knows the appropriate one or more frequencies to use to generate one or more stimulation signals.

Input device 314 can change at least one stimulation frequency as a result of a spectral analysis scan. In a synchronous system, a spectral analysis scan can execute while input device 314 is predicted to not be generating a stimulation signal, e.g., when an input device scan is not executing. After completing the spectral analysis scan, the frequency information can be communicated wirelessly to input device 314 and the communication can cause the input device to change the one or more stimulation frequencies. The base device can then switch the one or more frequencies used for demodulating scan events when input device 314 has switched frequencies.

In other examples, input device 314 can be asynchronous such that the input device can generate one or more stimulation signals at one or more stimulation frequencies irrespective of the timing of the scan event. As a result, input device 314 can be stimulating the touch sensor panel during the spectral analysis scan. The asynchronous stimulation signals can cause the base device to detect a signal when demodulating at the frequency of stimulation, which can be interpreted as noise at that frequency and trigger a frequency switch. In order to prevent triggering an unnecessary frequency switch, in embodiments where input device 314 is a stylus, the base device can assume that stylus lift-off will eventually occur and wait until lift-off to initiate a spectral analysis scan. The base device can predict a lift-off condition using the results of other scans, e.g., stylus scans, or stylus force information to predict that the stylus is not on the panel, and then perform a stylus spectral analysis scan.

Additionally, or alternatively, input device 314 can include additional sensors 396. Additional sensors 396 can include a capacitive electrode or other capacitive sensor (e.g., sensors 264 of FIG. 2), one or more temperature sensors, and one or more motion or orientation sensors, such as an IMU. For example, input device 314 can include an accelerometer and/or gyroscope to track motion and/or orientation of the input device, which can be used to augment input device position data when detected by a touch-sensitive surface. The motion and/or orientation information can be stored in memory 348 and/or transferred to the base device via wireless communication circuitry 350. Additionally, or alternatively, additional sensors 396 of input device 314 can include a camera to record images or video that can be used to determine the position of the input device and/or track the motion of the input device.

In embodiments where input device 314 is a stylus, due to the relative density of components within shaft portion 380 and tip portion 382, the shaft portion and the tip portion may not be well suited to include components required for the generation of an acoustic signal as described herein. In particular, certain components can be particularly sensitive to interference from other components or environmental effects, and can require dedicated or component-specific housing structures within input device 314. As an example, force sensor 358 that is coupled to tip portion 382 can be sensitive to environmental effects, and can therefore be provided a dedicated housing structure within shaft portion 380 and/or tip portion 382 that cannot be modified (e.g., the dedicated housing structure for force sensor 358 cannot be modified to integrate acoustic resonator(s) 394 without compromising the accuracy/reliability of force sensor 358). Similarly, at least a portion of shaft portion 380 can contain component-specific housing structures used to sense or detect user input (e.g., touch sensing, flex sensing, etc.) and can be sensitive to (or generally, precluded from) modifications. Additionally, at least a portion of shaft portion 380 can be used to house magnets and/or a wireless charging coil and can therefore be sensitive to modifications. As a result, the most suitable location within input device 314 for modifications such as the formation of acoustic resonator(s) 394 may be optional end/cap portion 352. At a second end of input device 314, end/cap portion 352 can include haptic module 392 and acoustic resonator(s) 394. Input device 314 can also include a battery or other power sources (not pictured) implemented at least partially in shaft portion 380 and/or end/cap portion 352 for delivering power to the powered components of input device 314. In general, while end/cap portion 352 is sometimes referred to as a different "end" of input device 314 than tip portion 382, the various portions of the input device can be considered to extend from distal ends, and even include them. As an example, considering a tip portion 382 as portion that extends from one of two distal ends of input device 314, end/cap portion 352 can be considered to extend from the opposite distal end of the input device. In general, input device 314 can be partitioned into first and second portions, with the first portion corresponding to tip portion 382 and shaft portion 380 that extend from a first distal end of the input device (e.g., the tip end), and with the second portion corresponding to end/cap portion 352 that extends from a second distal end of the input device (e.g., the cap end) that opposes the first distal end.

Acoustic resonator(s) 394 within end/cap portion 352 can describe one or more surfaces that are at least partially surrounded by air or an air gap, and can vibrate to generate an acoustic signal. In some examples, acoustic resonator(s) 394 can be surfaces engineered/designed to resonate at a particular resonant frequency. In other examples, acoustic resonator(s) 394 can be surfaces engineered/designed to resonate within a particular range of frequencies. Additionally, or alternatively, acoustic resonator(s) 394 can be mechanically coupled to haptic module 392 (e.g., the resonator(s) and the module can be coupled via a continuous path of material between them). In some examples, acoustic resonator(s) 394 can be separated from haptic module 392 by an air gap. In some examples, acoustic resonator(s) 394 can be formed from the same material used to form the housing of input device 314. In some examples, acoustic resonator(s) 394 can be formed from acrylonitrile butadiene styrene (ABS) plastic or polymer, a non-ABS plastic or polymer, or any other suitable material.

Acoustic resonator(s) 394 can be configured to vibrate in response to receiving a drive signal or a harmonic forcing signal. In the context of the current disclosure, the drive signal provided to acoustic resonator(s) 394 can originate from haptic module 392 and the vibrations caused by the haptic module. Vibrations generated at haptic module 392 can be conveyed, transmitted, or otherwise transmitted through such intervening structures to vibrate the acoustic resonator(s) 394. In some examples, acoustic resonator(s) 394 vibrate at the same frequency, amplitude, and duration as the vibrations generated at haptic module 392. In other examples, acoustic resonator(s) 394 vibrate at a different frequency and amplitude than the vibrations generated at haptic module 392 (e.g., due to transmission losses of the drive signal through structures/media that intervene between the module and the resonator(s)). When acoustic resonator(s) 394 are formed from rigid or semi-rigid materials, vibrations (and the corresponding acoustic signals) are created by clastic deformation of the materials.

Based on where in end/cap portion 352 acoustic resonator(s) 394 are formed, and the material used to form the resonator(s), a drive signal provided to the resonator(s) can cause the resonator(s) to vibrate according to one or multiple modes. In some examples, some vibration modes can correspond to highly directional acoustic signals (e.g., acoustic signals that can be easily sensed from a particular direction, but that can be harder to sense from other directions). In other examples, some vibration modes can correspond to omni-directional acoustic signals (e.g., acoustic signals that can be sensed from any direction). Some acoustic resonator(s) 394 can be formed so one of their surfaces is exposed to air, and the resonator(s) vibrations (or elastic deformations) cause sound waves to be produced in the air surrounding input device 314. Other acoustic resonator(s) 394 can be formed underneath other structures within input device 314 (e.g., underneath a cap of the input device). In some such examples, resonator(s) 394 can cause sound waves to be produced in the surrounding air within the other structures. As described below in greater detail, some coverings for resonator(s) 394 in end/cap portion 352 can completely cover the resonator, and other coverings can substantially (e.g., greater than a threshold amount, such as 80%, 90%, 95%, 98%) cover resonator(s) 394 in the end/cap portion without completely covering them (e.g., due to a ventilating hole in the covering that allows sound waves produced by the resonator to escape outside of the housing of the input device).

Haptic module 392 can also be disposed or housed within end/cap portion 352, and can be coupled to acoustic resonator(s) 394. Haptic module 392 can receive instructions for vibrating in a manner such that acoustic resonator(s) 394, which can be mechanically coupled to the haptic module, vibrate at a specified frequency, amplitude, and/or duration. In some examples, the instructions for vibrating haptic module 392 can be based on the location request received at wireless communication circuitry 350 (e.g., from base device 216 of FIG. 2). Structurally, haptic module 392 can include a mass that vibrates between two locations within the module. In some examples, instructions for vibrating haptic module 392 causes electromagnetic forces (e.g., Lorentz forces) to vibrate the mass between the two locations within the module. The vibrations of haptic module 392 can be transferred or transmitted to acoustic resonator(s) 394, either through one or more air gaps or through a contiguous path of material that mechanically couples the module to the resonator(s).

In some examples, haptic module 392 can vibrate in a manner such that acoustic resonator(s) 394 do not vibrate at all, or instead vibrate in a manner such that the resonator(s) do not produce an acoustic signal (or produced an acoustic signal below a threshold level). In some such examples, such as during a default mode of input device 314, haptic module 392 can be configured to vibrate at frequencies outside an audible range of frequencies associated with human hearing. Specifically, haptic module 392 can be configured to vibrate at frequencies within a range of frequencies associated with haptic feedback, such as at frequencies less than 500 Hz. In some examples, haptic module 392 can be configured to vibrate at frequencies in the range of 80 Hz-300 Hz. Haptic module 392 can be configured to receive instructions to vibrate at frequencies within the range of frequencies associated with haptic feedback in the default mode in response to a gesture performed by the user using input device 314, a user selection on a touch-sensitive surface of a base device using the input device, or in accordance with any other determination during a default mode of operation associated with the input device.

In a beacon mode, haptic module 392 can vibrate in a manner such that acoustic resonator(s) 394 vibrate to generate an acoustic signal. In some examples, haptic module 392 can sometimes receive instructions from a location request (e.g., a request from an electronic device for input device 314 to generate an acoustic signal) that specify a target detector. A target detector can indicate which range of frequencies should be used to select a frequency for vibrating haptic module 392. Generally, input device 314 can generate an acoustic signal that can be detected by base devices and/or a user. However, a target detector specified in the location request can narrow the frequency range selected at which to vibrate haptic module 392 to optimize/improve detection by the target detector. In some examples, the target detector specified in the location request is a user. In some such examples, haptic module 392 can be configured to vibrate at frequencies within an audible range of frequencies associated with human hearing. Alternatively, haptic module 392 can be configured to vibrate at frequencies within a sub-range of the audible range of frequencies associated with human hearing. In some examples, the target detector specified in the location request is a base device. In some such examples, haptic module 392 can be configured to vibrate at frequencies within a range of frequencies that an acoustic or ultrasonic transducer (e.g., ultrasonic sensor 240 shown in FIG. 2) within the device can accurately/optimally detect. In some such examples, haptic module 392 can additionally or alternatively be configured to vibrate at frequencies within a range that the acoustic transducer can detect using less power (e.g., ranges within the frequency spectrum which require less amplification of the acoustic transducer/sensor output to produce a reliably detectable signal). In some such examples, haptic module 392 can additionally or alternatively be configured to vibrate at frequencies within a range that the acoustic transducer can detect with less noise (e.g., ranges within the frequency spectrum the acoustic transducer/sensor can detect with a high signal-to-noise ratio, or with a higher time interval between false-positive signal detections due to environmental noise). Sometimes, the range of frequencies that an acoustic transducer can accurately detect can be different from, or even partially outside the audible range of frequencies, or any sub-range of the audible range. Therefore, the range of frequencies that an acoustic transducer can accurately detect can sometimes be considered to be an inaudible range of frequencies. Generally then, the range of frequencies that an acoustic transducer can accurately detect may not be entirely inaudible for human hearing (e.g., the range associated with the transducer can at least partially overlap the audible range) or may not be entirely within the audible range of frequencies associated with human hearing (e.g., the range associated with the transducer is not a proper subset or sub-range of the audible range).

It is to be understood that input device 314 is not limited to the components and configuration of the stylus shown in FIG. 3, but can include other, fewer or additional components in multiple configurations according to various examples. Additionally, the components of input device 314 can be included within a single device or can be distributed between multiple device portions. For example, in embodiments where input device 314 is a stylus, the input device can include an end/cap portion 352, shaft portion 380 and tip portion 382. In some examples, input device 314 can include removable stylus tip portion 382, so that the tip portion can be removed and replaced when necessary or to enable different functionality. Removable tip portion 382 and shaft portion 380 can be coupled together with a connector (not shown). For example, the connector can be a threaded screw-type connector, plug-in connector, or the like. In some examples, a locking or fastening system between removable stylus tip portion 382 and shaft portion 380 can include a fastening bar, spring fastener and a release button. Removable tip portion 382 can include one or more electrodes 384 (e.g., for stimulating a capacitive sensor panel). Many of the remaining components can be included, as illustrated, in shaft portion 380. It should be understood that the various components can be distributed in different ways between shaft portion 380 and tip portion 382. Additionally, it should be understood that components of a stylus (or other peripheral/input device) may be implemented in an otherwise passive stylus such that components used for touch detection proximate to a touch-sensitive surface can be omitted (e.g., stylus stimulation circuitry 390).

As alluded to above, a majority of components associated with embodiments where input device 314 is a stylus can be disposed or otherwise located within shaft portion 380 and tip portion 382. As such, including haptic module 392 and/or acoustic resonator(s) 394 within these portions of input device 314 may result in interference with densely distributed circuitry and components. Therefore, haptic module 392 and acoustic resonator(s) 394 can be included or disposed within an end/cap portion 352 of input device 314 that is separate from shaft portion 380, thereby reducing the risk of resonator(s) 394 and/or the module interfering with any of the components therein.

Figure 4A:
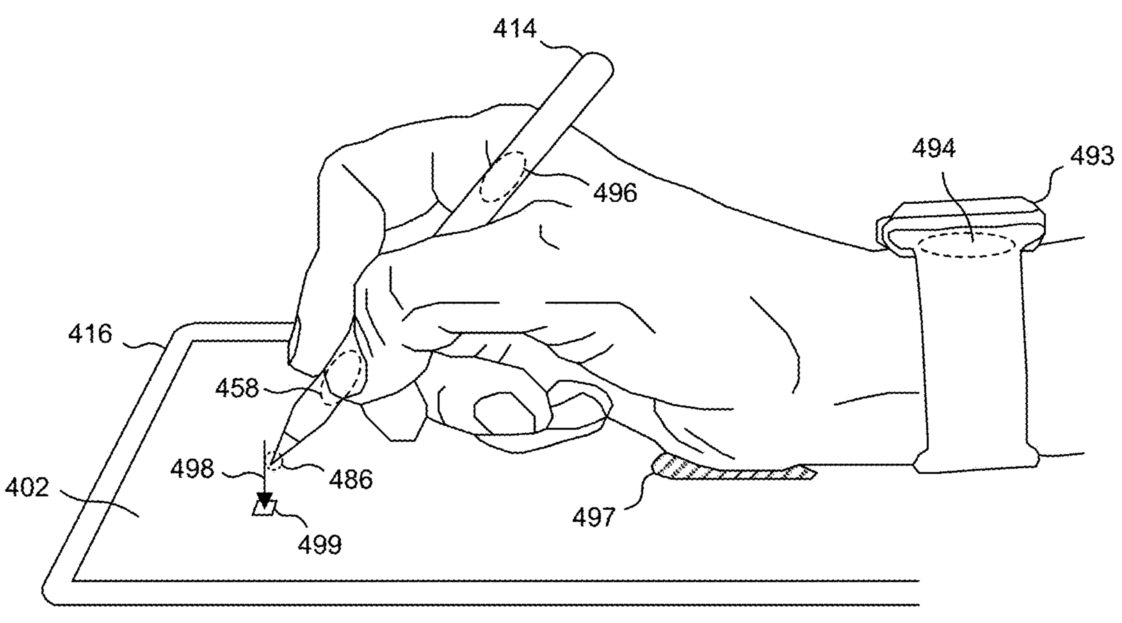
FIG. 4A illustrates a perspective view of a system including an input device in the form of a stylus, an optional base device in the form of a tablet computing device, and an optional wearable device in the form of a watch for providing wellness insights to a user according to some examples of the disclosure.

FIG. 4A illustrates a perspective view of a system including input device 414 in the form of a stylus, optional base device 416 in the form of a tablet computing device, and optional wearable device 493 in the form of a watch for providing wellness insights to a user according to some examples of the disclosure. In the example of FIG. 4A, input device 414 includes one or more force sensors 458 and temperature sensor 496 on the sides of the input device, and tip electrode 486 at the tip of the input device. Although not shown in FIG. 4A, input device 414 can also include a force sensor at the tip of the input device for detecting force 498 normal to touch screen 402 of base device 416. Base device 416 can include touch screen 402, among other sensors. Wearable device can include photoplethysmography (PPG) sensor 494, among other sensors.

Figure 4B:
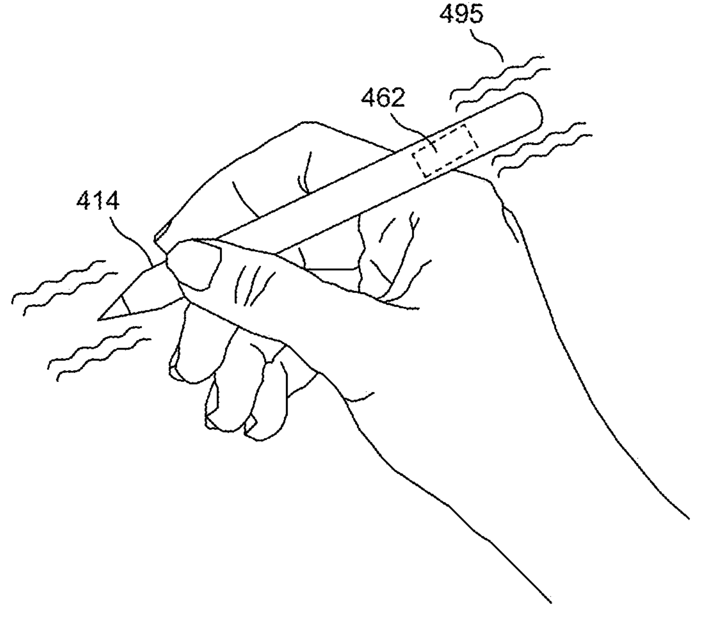
FIG. 4B illustrates a perspective view of an input device in the form of a stylus being held in a user's hand for providing wellness insights to a user according to some examples of the disclosure.

FIG. 4B illustrates a perspective view of input device 414 in the form of a stylus being held in a user's hand for providing wellness insights to a user according to some examples of the disclosure. In the example of FIG. 4B, input device further includes IMU 462 for detecting and/or calculating one or more of force, angular rate, acceleration, pitch, roll, yaw, velocity, tilt, etc. IMU 462 can include one or more of accelerometers, gyroscopes, and magnetometers.

With the sensors and other measurement devices present in input device 414, optional base device 416, and optional wearable device 493 as shown in the ecosystem of FIGS. 4A and 4B and described above, data can be captured as directed by a wellness tracking application executed by a processor in either or both of the base device and/or input device of FIG. 2, which can be used to generate and update a user profile. In some examples, force sensors 458 on the sides of input device 414 can capture data related to how much pressure or force a user is applying to the input device (e.g., grip pressure or grip strength) as the user writes or draws with the input device. In some examples, grip pressure can range from about 80-300 gram force (gf), although it should be understand that the grip pressure can vary greatly from one user to another. In addition, in some examples a plurality of force sensors 458 can be located on the sides (barrel) of input device 414, and these force sensors can capture data that can enable the touch locations (e.g., a contact area or distribution of contacts) of the user's grip to be determined. Because of the consistent manner in which a user will typically hold input device 414, in some examples the determined distribution of contacts can become part of the user's profile. Similarly, in some examples, data sufficient to determine a tilt angle of input device 414 can be captured using IMU 462. Because of the consistent manner in which the user will typically hold input device 414, in some examples the determined tilt angle can become part of the user's profile.

The force sensor optionally located at the tip of input device 414 can be utilized to determine how much normal force the user applies to base device 416 when using the input device to write or draw on touch screen 402, although in other examples force sensors in base device 416 may alternatively additionally be used to determine the force being applied to the base device. In addition, temperature sensor 496 can be utilized to determine the temperature of the user while input device 414 is being held by the user. IMU 462 can also be utilized to determine and/or calculate parameters sufficient to determine whether vibrations 495 are being felt in input device 414 due to tremors in a user's hand.

As noted above, base device 416 can include touch screen 402. Touch screen 402 can include an array of touch and/or force sensors for detecting the touch location and/or force of input device 414 upon the touch screen at 499, and also the touch locations and/or force of the palm of a user's hand upon the touch screen at 497.

PPG sensor 494 in the watch of FIG. 4A can be utilized to capture blood volume measurements and measure the user's heart rate and other biometric data.

In some examples, the above-described data capture using the sensors and other measurement electronics of input device 414, optional base device 416, and optional wearable device 493 can be captured passively and automatically as directed by the wellness tracking application, without user input, during everyday use of the input device (e.g., writing or drawing). Passive data capture during normal usage of input device 414 can advantageously avoid the potential for data corruption due to unintended and imperceptible alterations in user behavior that can occur when the user is made aware of an impending data capture. In other examples, the user can be prompted (via a display screen of base device 416, wearable device 493, etc.) to perform certain tasks (e.g., draw specific shapes or letters, or follow a provided contour) to assist in capturing the data.

As data is collected as described above, a user profile including baseline profile data can be created, tracked and updated over time by the wellness tracking application to provide insights into a user's wellness. The time period of the data capture can be viewed as consisting of two time periods. One time period can be a current (first) time period, which may not be an instantaneous point in time, but rather a short period of time just preceding the present time when "current" data can be captured, computed and converted into short-duration averages, scores or other parameters. Another time period can be a historical (second) time period, which can be a longer period of time preceding the current time period when "historical" data can be captured, averaged, and/or converted to various scores.

In some examples, the user profile can include a hand profile which can be created, tracked and updated under the assumption that a user tends to grip input device 414 in a consistent manner with every use, although in certain instances multiple hand profiles may be needed for a single user if the user prefers different grips depending on the type of activity (e.g., drawing versus writing). In some examples, the hand profile can include one or more of an average palm pressure and palm contact area detected on base device 416, an average input device tip pressure detected at a tip of the input device 414, an average grip pressure detected on a side of the input device, the location, size and distribution of grip contacts detected on a side of the input device, the tilt angle of the input device, and the average temperature detected at the input device.

In some examples, the user profile can include a writing behavior profile which can be created, tracked and updated under the assumption that a user tends to write in a consistent manner. The writing behavior profile can include baseline information on a user's everyday writing tendencies, independent of tendencies within individual strokes. For example, the writing behavior profile can include the user's average stroke count per minute, which is an indication of how fast the user writes. Other writing behavior profile data can include the user's average words per minute, or the average time between strokes, or between words. In some examples, the writing behavior profile can include higher level information such as how often the user corrects their writing, or how often a user's words are autocorrected. Additionally, the frequency at which a user switches between an on-screen (virtual) keyboard and writing with hand-held input device 414 can be tracked as a possible metric useful in determining a user's wellness state. In another example, the frequency at which a user zooms in or out on a touch screen display (in order to write comfortably) can be tracked as a possible metric useful in determining a user's wellness state.

In some examples, the user profile can include a stroke analysis profile which can be created, tracked, and updated under the assumption that a user tends to form strokes in a consistent manner when writing. The stroke analysis profile can include baseline information on a user's tendencies when forming individual strokes. For example, the stroke analysis profile can include the user's average stroke speed, which captures the speed of the motion of individual strokes. The stroke analysis profile can also include the user's average stroke size, which captures the size of individual strokes.

In some examples, the stroke analysis profile can receive, track and update information from other tools, such as the character recognition speed of a user's strokes using a handwriting recognition application. Character recognition can involve the capture and preprocessing of stroke data to discard unwanted information, the extraction of feature data including pressure, velocity and/or directional data from the stroke data, and the mapping of the feature data to various characters. The stroke analysis profile can determine how long it took to perform the character recognition, and may also assign a score indicative of how well-matched the user's strokes were to the recognized letter, number or punctuation mark.

Figure 5A:
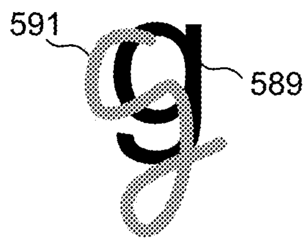
FIG. 5A illustrates the recognition of a single character for providing wellness insights to a user according to some examples of the disclosure.

FIG. 5A illustrates the recognition of a single character for providing wellness insights to a user according to some examples of the disclosure. In the example of FIG. 5A, the user has written character 591 on a base device using an input device. A handwriting recognition application can detect stroke information such as the location, pressure, velocity and direction of each stroke made by the user in writing character 591, and after the preprocessing, feature extraction and mapping described above, the stroke(s) can be mapped to a lowercase letter "g" 589 as shown in FIG. 5A. The speed of the character recognition can be determined, and a score may be assigned indicative of how well matched the handwritten character 591 was to the recognized letter 589.

In some examples, the stroke analysis profile can include the creating, tracking and updating of the user's compliance with predefined tasks. For example, a wellness tracking application can initiate a contour tracking task. Once initiated, the contour tracking task can display a request on the touch screen of a base device to trace a line or other contour appearing on the touch screen, map the user-generated stroke(s) to the displayed line or contour, and may assign a contour tracking score indicative of how well-matched the user's strokes were to the line or contour. In some instances, the wellness tracking application can be programmed to initiate the contour tracking task once a day, once a week, once a month, or other pre-selected time interval. The contour tracking score can be saved and averaged with previous contour tracking scores.

Figure 5B:
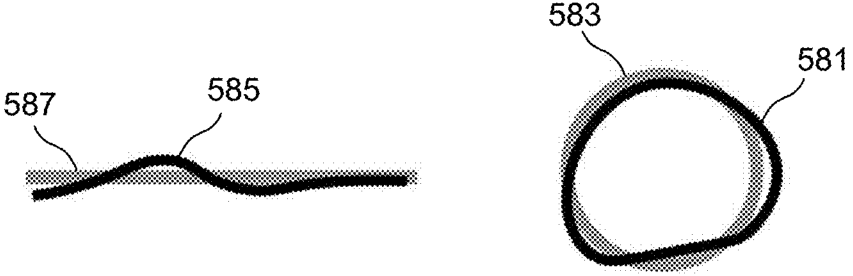
FIG. 5B illustrates two different contour tracking tasks for providing wellness insights to a user according to some examples of the disclosure.

FIG. 5B illustrates two different contour tracking tasks for providing wellness insights to a user according to some examples of the disclosure. In the first example of FIG. 5B, a wellness tracking application has initiated a contour tracking task and has displayed contour 587, a straight line, along with a request for the user to follow the contour using an input device. In response, the user has generated stroke 585. In the second example of FIG. 5B, a wellness tracking application has initiated a contour tracking task and has displayed contour 583, a circle, along with a request for the user to follow the contour using an input device. In response, the user has generated stroke 581. In both examples, the contour tracking task can compute and save a contour tracking score, and utilize this score to maintain and update a baseline contour tracking score (e.g., by computing and saving a running average contour tracking score).

In another example, the wellness tracking application can initiate a hand stability tracking task. Once initiated, the hand stability tracking task can display a request on the touch screen of a base device for the user to hold an input device in the air, capture stability data using an IMU in the input device, and assign a hand stability score indicative of the stability of the user's hand. In some instances, the wellness tracking application can be programmed to initiate the hand stability tracking task once a day, once a week, once a month, or other pre-selected time interval. The hand stability tracking score can be saved and averaged with previous hand stability tracking scores.

In some examples, the user profile can include a wearable device profile which can be created, tracked and updated under the assumption that when a user wears wearable device 493, the user tends to wear the wearable device in a consistent manner with every use. In some examples, the wearable device profile can include the user's average and/or historical heart rate data, along with the average and/or historical data for other biometric parameters.

Figure 6:
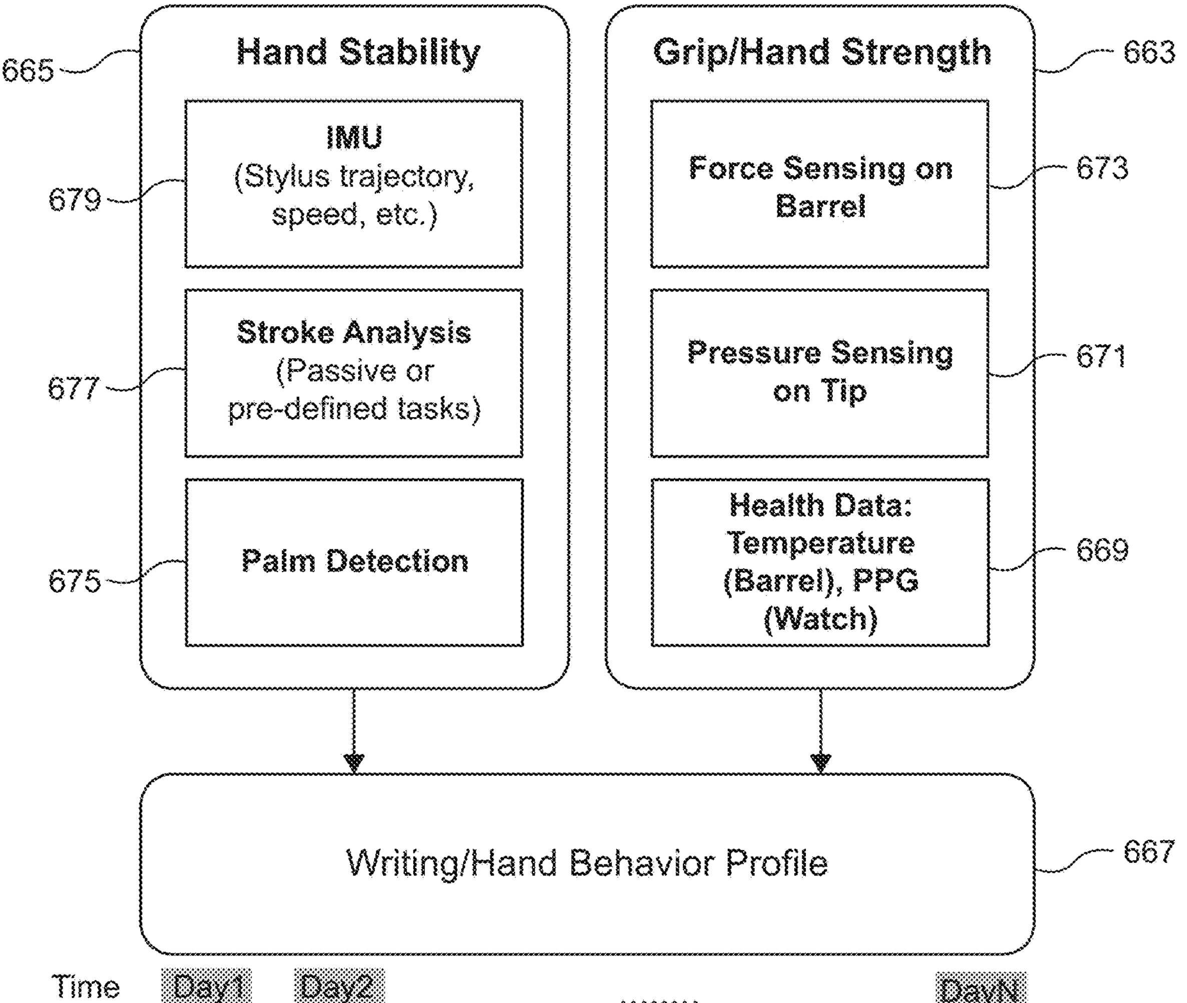
FIG. 6 illustrates a functional block diagram of data collection for the user profile generation and maintenance described above according to some examples of the disclosure.

FIG. 6 illustrates a functional block diagram of data collection for the user profile generation and maintenance described above according to some examples of the disclosure. In the example of FIG. 6, a user profile can be generated and maintained through hand stability data collection 665 and grip/hand strength data collection 663. Hand stability data collection 665 can include the collection of IMU data 679, which can include data that can be used to determine the speed, acceleration, motion (e.g., trajectory, including direction) of an input device in space, and other movement-related parameters. Hand stability data collection 665 can also include stroke analysis data collection 677, which can include the passive collection and computation of stroke speed, stroke size/length, average stroke force, character recognition time, and character matching accuracy. Stroke analysis data collection 677 can also include the active computation and tracking of a contour tracking score based on pre-defined tasks such as the tracing of a displayed line or other contour using an input device. Palm detection data collection 675 can include the determination of palm contacts and palm pressure on a touch-sensitive surface of a base device.

Grip/hand strength data collection 663 can include force sensing data collection 673, including the collection of grip pressure and grip locations on the sides of an input device, and tip pressure sensing data collection 671, which includes the determination of the pressure applied to a base device by the input device. Grip/hand strength data collection 663 can also include health data collection 569, which can include the collection of temperature data from one or more temperature sensors on the barrel of the input device, and the collection of data from other associated devices such as the data from a PPG sensor on a wearable device.

The data from hand stability data collection 665 and grip/hand strength data collection 663 form the basis for generating and maintaining writing/hand behavior profile 667 as described above. In some examples, data can be collected each time the input device is detected as being gripped by a user, and writing/hand behavior profile 667 can be updated on a periodic basis (e.g., daily, weekly, monthly, etc.) via the computation of new baseline average values on a rolling basis (e.g., using data from the last week, from the last month, etc.).

As the user profile is generated, maintained, and updated as described above, newly collected data can be periodically compared to baseline user profile data by the wellness tracking application to identify any deltas or changes between the newly collected data and the baseline profile data that exceed predetermined thresholds. If such data is identified, wellness insights or alerts can be provided to the user. These periodic comparisons can be performed at predetermined intervals, such as daily, weekly, monthly, quarterly, yearly, etc. For example, newly collected data can be compared to baseline user profile data from a day ago, a week ago, a month ago, a quarter ago, a year ago, etc. In this manner, gradual but significant changes to a user's profile, which might not be detectable in short-duration comparisons (e.g., day-to-day comparisons, week-to-week comparisons, etc.), can be detected and provided to the user as a wellness insight.

Although the preceding paragraphs describe the computation of updated baseline user profile data, in some examples on a rolling basis (e.g., using data from the last week, from the last month, etc.), and also storing snapshots of previous baseline user profile data (e.g., from a day ago, a week ago, etc.) for use in future comparisons, in other examples the wellness tracking application can provide the user with the ability to re-baseline their user profile data. For example, a user can delete their current baseline user profile data and rely upon subsequent data captures to compute new baseline user profile data. This process of re-baselining user profile data may be useful in situations of illness, injury, or other known event that could lead to a behavior change such that baseline user profile data reflective of a user's prior (e.g., healthy) condition may be of limited probative value when compared to newly collected data reflective of the user's current (e.g., sick or injured) condition.

It should be noted that significant changes to a user's profile can be cause for optimism or concern. For example, significant changes to a child's profile, or significant changes to the profile of a person recovering from an illness, injury, or surgery, may be indicative of improvement rather than decline, and as such, the wellness tracking application can provide wellness insights that are encouraging. In one specific example, a user profile of a child can be generated, maintained, and updated as described above, and newly collected data such as grip strength data and/or handwriting recognition score or speed data can be periodically compared to baseline user profile data and analyzed by the wellness tracking application to identify any deltas or changes between the newly collected data and the baseline profile data that exceed predetermined thresholds. If such data is identified, wellness insights of encouragement or congratulation related to the hand or writing development of the child can be provided to the child and/or a responsible adult (if contact information is available). On the other hand, significant changes to the user profile of others, especially changes in a direction that is normally viewed as a concern, can cause the wellness tracking application to provide wellness insights in the form of alerts.

In some examples, a change to a user's nominal grip pressure that exceeds a predetermined threshold (e.g., a particular fixed threshold value, or a particular threshold percent change) can trigger the generation of a wellness insight to the user. In one example, a measured grip pressure below a particular level (e.g., below 80 gf, 60 gf, 40 gf, etc.) or a measured grip pressure greater than a predetermined percent reduction as compared to the baseline grip pressure (e.g., greater than 10% lower, 20% lower, 30% lower, etc.) can trigger the generation of a wellness insight to the user indicating hand weakness. Note that the fixed threshold value or the threshold percent change in grip pressure can depend on the nominal baseline grip pressure. For example, the threshold percent change in grip pressure that triggers the generation of a wellness insight can be larger for a user with a nominal grip pressure of 300 gf than a user with a nominal grip pressure of 80 gf. In addition, the threshold percent change in grip pressure can depend on the form factor of the input device (e.g., the thickness of a stylus), so the determination of a threshold percent change in grip pressure sufficient to trigger the generation of a wellness insight may be a function of the form factor of the input device. Note that in some examples, a change to a user's nominal grip pressure that exceeds a threshold may trigger the generation of a wellness insight independent of other changes, while in other examples a change to a user's nominal grip pressure that exceeds the threshold may only trigger the generation of a wellness insight when one or more other values in the user's profile also exceed a threshold.

In some examples, a change to a user's nominal grip contact area that exceeds a predetermined threshold (e.g., a particular fixed threshold value, or a particular threshold percent change) can trigger the generation of a wellness insight to the user. In one example, a measured grip contact area below a particular level (e.g., below 1.5 $cm^2$, 1.25 $cm^2$, 1.0 $cm^2$, etc.) or a measured grip contact area greater than a predetermined percent reduction as compared to the baseline contact area (e.g., greater than 10% lower, 20% lower, 30% lower, etc.) can trigger the generation of a wellness insight to the user indicating hand weakness (e.g., causing less grip pressure and therefore less contact area). Note that the fixed threshold value or the threshold percent change in grip contact area can depend on the form factor of the input device (e.g., the thickness of a stylus), so the determination of a threshold percent change in grip contact area sufficient to trigger the generation of a wellness insight may be a function of the form factor of the input device. Note that in some examples, a change to a user's nominal grip contact area that exceed a threshold may trigger the generation of a wellness insight independent of other changes, while in other examples a change to a user's nominal grip contact area that exceeds the threshold may only trigger the generation of a wellness insight when one or more other values in the user's profile also exceed a threshold.

In some examples, a change to the nominal tilt angle at which a user holds an input device (e.g., a stylus) that exceeds a predetermined threshold (e.g., a particular fixed threshold value, or a particular threshold percent change) can trigger the generation of a wellness insight to the user. In one example, a measured tilt angle above a particular level (e.g., above 60 degrees, above 70 degrees, above 80 degrees, etc.) or a measured tilt angle greater than a predetermined percent increase as compared to the baseline tilt angle (e.g., greater than a 10% increase, greater than a 20% increase, greater than a 30% increase, etc.) can trigger the generation of a wellness insight to the user indicating hand weakness or injury (e.g., causing the user to compensate for a lack of stylus pressure on the base device by increasing the tilt angle). Note that in some examples, a change to a user's stylus tilt angle that exceeds a threshold may trigger the generation of a wellness insight independent of other changes, while in other examples a change to a user's stylus tilt angle that exceeds the threshold may only trigger the generation of a wellness insight when one or more other values in the user's profile also exceed a threshold.

In some examples, a change to the nominal hand stability score at which a user typically holds an input device (e.g., a stylus) that exceeds a predetermined threshold (e.g., a particular fixed threshold value, or a particular threshold percent change) can trigger the generation of a wellness insight to the user. In one example, a computed hand stability score below a particular level (e.g., below a normalized 1-100 score of 70, 60, 50, etc.) or a computed hand stability score less than a predetermined percent decrease as compared to the baseline hand stability score (e.g., greater than a 10% decrease, greater than a 20% decrease, greater than a 30% decrease, etc.) can trigger the generation of a wellness insight to the user indicating hand instability (e.g., due to stress, anxiety, or Parkinson's disease). Note that in some examples, a change to a user's hand stability score that exceeds a threshold may trigger the generation of a wellness insight independent of other changes, while in other examples a change to a user's stylus tilt angle that exceeds the threshold may only trigger the generation of a wellness insight when one or more other values in the user's profile also exceed a threshold.

In some examples, a change to the nominal hand temperature of a user holding an input device (e.g., a stylus) that exceeds a predetermined threshold (e.g., a particular fixed threshold value, or a particular threshold percent change) can trigger the generation of a wellness insight to the user. In one example, a measured hand temperature below or above a particular level (e.g., below 98.4 degrees, below 98.2 degrees, above 100 degrees, above 101 degrees, etc.) or a measured hand temperature greater or less than a predetermined percent increase or decrease as compared to the baseline hand temperature (e.g., greater than a 1% increase/decrease, greater than a 2% increase/decrease, etc.) can trigger the generation of a wellness insight to the user indicating possible stress, anxiety or illness. Note that in some examples, a change to a user's hand temperature that exceeds a threshold may trigger the generation of a wellness insight independent of other changes, while in other examples a change to a user's temperature that exceeds the threshold may only trigger the generation of a wellness insight when one or more other values in the user's profile also exceed a threshold.

In some examples, a change to the nominal pressure and/or contact area of a user's palm against a base device while holding an input device (e.g., a stylus) that exceeds a predetermined threshold (e.g., a particular fixed threshold value, or a particular threshold percent change) can trigger the generation of a wellness insight to the user. In one example, a measured palm pressure above a particular level (e.g., above 100 gf, above 300 gf, above 500 gf, etc.) or a measured palm contact area above a particular value (e.g., greater than 1.5 $cm^2$, greater than 2 $cm^2$, greater than 2.5 $cm^2$, etc.), or a measured palm pressure increase greater than a predetermined percent increase as compared to the baseline palm pressure (e.g., greater than a 5% increase, greater than a 10% increase, etc.) or a measured palm contact area increase greater than a predetermined percent increase as compared to the baseline palm contact area (e.g., greater than a 5% increase, greater than a 10% increase, etc.) can trigger the generation of a wellness insight to the user indicating possible stress or anxiety (e.g., causing tension that produces more palm pressure and/or contact area). Note that in some examples, a change to a user's palm pressure or contact area that exceeds a threshold may trigger the generation of a wellness insight independent of other changes, while in other examples a change to a user's palm pressure or contact area that exceeds the threshold may only trigger the generation of a wellness insight when one or more other values in the user's profile also exceed a threshold.

In some examples, a change to the nominal pressure of a tip of an input device (e.g., a stylus) against a base device that exceeds a predetermined threshold (e.g., a particular fixed threshold value, or a particular threshold percent change) can trigger the generation of a wellness insight to the user. In one example, a measured tip pressure above a particular level (e.g., above 5 gf, above 10 gf, above 20 gf, etc.), or a measured tip pressure increase greater than a predetermined percent increase as compared to the baseline tip pressure (e.g., greater than a 5% increase, greater than a 10% increase, etc.) can trigger the generation of a wellness insight to the user indicating possible stress, anxiety or illness (e.g., causing tension that produces more tip pressure upon the base device). Note that in some examples, a change to the input device tip pressure upon a base device that exceeds a threshold may trigger the generation of a wellness insight independent of other changes, while in other examples a change to the input device tip pressure upon a base device that exceeds the threshold may only trigger the generation of a wellness insight when one or more other values in the user's profile also exceed a threshold.

In some examples, changes to the user's writing behavior profile (e.g., changes to the user's average stroke count per minute, average number of words per minute, average time between strokes, average time between words) that exceed a predetermined threshold (e.g., a particular fixed threshold value, or a particular threshold percent change) can trigger the generation of a wellness insight to the user. In some examples, a measured and computed average stroke count per minute below a particular level (e.g., below 150 strokes/minute, below 100 strokes/minute, etc.), or a measured and computed average number of words per minute below a particular level (e.g., below 60 words/minute, below 30 words/minute, etc.), or a measured and computed average time between strokes above a particular level (e.g., above 200 milliseconds (ms), above 500 ms, etc.), or a measured and computed average time between words above a particular level (e.g., above 500 milliseconds (ms), above 1 s, etc.) can trigger the generation of a wellness insight to the user indicating possible stress, anxiety, cognitive decline or illness. Similarly, a measured and computed average stroke count per minute, average number of words per minute, average time between strokes, or average time between words greater or less than a predetermined percent increase as compared to the baseline values (e.g., greater than a 5% increase/decrease, greater than a 10% increase/decrease, etc.) can trigger the generation of a wellness insight to the user indicating possible stress, anxiety, cognitive decline or illness. Note that in some examples, a change to the user's average stroke count per minute, average number of words per minute, average time between strokes, or average time between words that exceeds a threshold may trigger the generation of a wellness insight independent of other changes, while in other examples these changes may only trigger the generation of a wellness insight when one or more other values in the user's profile also exceed a threshold.

In some examples, other changes to the user's writing behavior profile (e.g., changes to how often a user corrects their writing, how often a user's words are autocorrected, the frequency at which a user switches between an on-screen (virtual) keyboard and writing with a hand-held input device, or the frequency at which a user zooms in or out on a touch screen display) that exceed a predetermined threshold (e.g., a particular fixed threshold value, or a particular threshold percent change) can trigger the generation of a wellness insight to the user. In some examples, a measured and computed average number of user corrections or autocorrection per minute above a particular level (e.g., above 5 corrections/minute, above 10 corrections/minute, etc.), or a measured and computed average number of virtual keyboard/handheld input device switches or zoom in/zoom out switches per minute above a particular level (e.g., above 0.5 switches/minute, above 1 switch/minute, etc.) can trigger the generation of a wellness insight to the user indicating possible stress, anxiety, cognitive decline or illness. Similarly, a measured and computed average number of user corrections or autocorrections per minute, or a measured and computed average number of virtual keyboard/handheld input device (e.g., input mode) switches or zoom in/zoom out (e.g., zoom ratio) switches per minute greater or less than a predetermined percent increase as compared to the baseline values (e.g., greater than a 5% increase/decrease, greater than a 10% increase/decrease, etc.) can trigger the generation of a wellness insight to the user indicating possible stress, anxiety, cognitive decline or illness. Note that in some examples, a change to the user's average number of user corrections or autocorrections per minute, or a measured and computed average number of virtual keyboard/handheld input device switches or zoom in/zoom out switches per minute that exceeds a threshold may trigger the generation of a wellness insight independent of other changes, while in other examples these changes may only trigger the generation of a wellness insight when one or more other values in the user's profile also exceed a threshold.

In some examples, changes to the user's stroke analysis profile (e.g., changes to the user's average stroke speed, average stroke size, average character recognition speed, average character matching score, average contour tracking score) that exceed a predetermined threshold (e.g., a particular fixed threshold value, or a particular threshold percent change) can trigger the generation of a wellness insight to the user. In some examples, a measured and computed average stroke speed below a particular level (e.g., below 5 cm/sec, below 2.5 cm/sec, etc.), a measured and computed average stroke size below a particular level (e.g., below 7 mm/stroke, below 5 mm/stroke, etc.), a measured and computed average character recognition speed of a longer duration than a particular level (e.g., longer than 0.25 sec, longer than 0.5 sec, etc.), or a measured and computed average character matching score or average contour tracking score lower than a particular level (e.g., below a normalized 1-100 score of 70, 60, 50, etc.) can trigger the generation of a wellness insight to the user indicating possible stress, anxiety, cognitive decline or illness (e.g., abnormally small or cramped handwriting can be an early sign of Parkinson's disease). Similarly, changes to the user's average stroke speed, average stroke size, average character recognition speed, average character matching score, or average contour tracking score greater or less than a predetermined percent change as compared to baseline values (e.g., greater than a 5% increase/decrease, greater than a 10% increase/decrease, etc.) can trigger the generation of a wellness insight to the user indicating possible stress, anxiety, cognitive decline or illness. Note that in some examples, a change to the user's average stroke speed, average stroke size, average character recognition speed, average character matching score, or average contour tracking score greater or less than a predetermined percent change that exceeds a threshold may trigger the generation of a wellness insight independent of other changes, while in other examples these changes may only trigger the generation of a wellness insight when one or more other values in the user's profile also exceed a threshold.

In some examples, changes to the user's wearable device (e.g., watch) profile (e.g., changes to the user's blood volume, heart rate, or other biometric parameters) that exceed a predetermined threshold (e.g., a particular fixed threshold value, or a particular threshold percent change), along with changes to other values in the user's profile that exceed predetermined thresholds, can trigger the generation of a wellness insight to the user. In some examples, a measured and computed heart rate above or below a particular level (e.g., above 120 bpm, above 140 bpm, below 55 bpm, below 50 bpm, etc.) can trigger the generation of a wellness insight to the user indicating possible stress, anxiety, illness or injury. Similarly, changes to the user's average measured and computed heart rate greater or less than a predetermined percent change as compared to baseline values (e.g., greater than a 5% increase/decrease, greater than a 10% increase/decrease, etc.) can trigger the generation of a wellness insight to the user indicating possible stress, anxiety, illness or injury.

As newly collected data is periodically compared to baseline user profile data, and deltas or changes between the newly collected data and the baseline profile data that exceed predetermined thresholds are identified, wellness insights can be provided to the user by the wellness tracking application. In some examples, a wellness insight (or an invitation to access the wellness insight) can appear as a textual message, dashboard and/or data presented on a base device (e.g., a tablet) or on an associated wearable device (e.g., a watch). In some examples, the wellness insight can provide information on what profile data has changed, when it changed (e.g., the time period of the detected change), and the amount of the change. The wellness insight can also provide content related to daily or monthly trends in the changed profile data, or other profile data that is currently changing (but perhaps not exceeding change thresholds), or information on single events (e.g., one-time changes to profile data that exceeded a threshold). However, it should be noted that in most examples, a wellness insight is a report on detected conditions, but is not a diagnosis as to the cause of those conditions, and is not intended as a tool to direct or recommend changes in a user's behavior.

Figure 7:
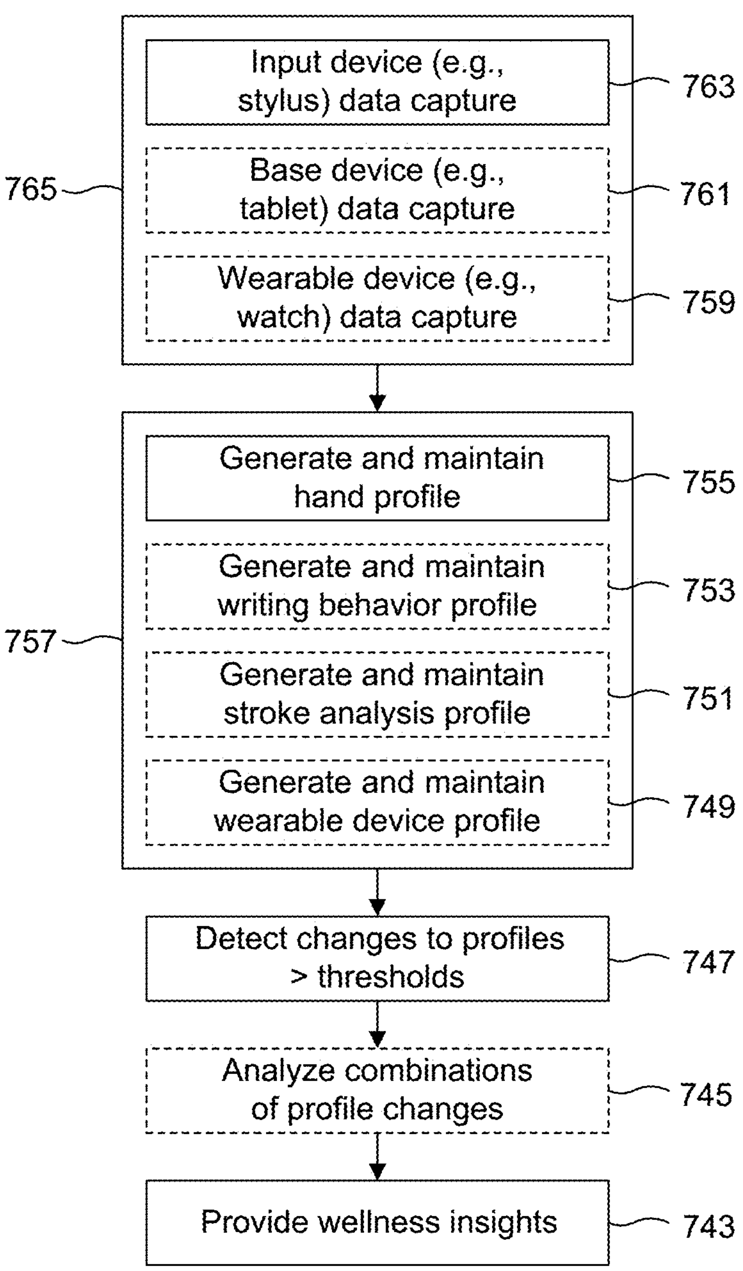
FIG. 7 illustrates a flowchart for generating user wellness insights using an input device such as a stylus according to some examples of the disclosure.

FIG. 7 illustrates a flowchart for generating user wellness insights using an input device such as a stylus according to some examples of the disclosure. In the example of FIG. 7, a wellness tracking application can perform data capture 765. Data capture at 765 can include data capture from an input device (e.g., input device 114 of FIGS. 1A-1E) at 763, and optionally can also include data capture from a base device (e.g., the devices of FIGS. 1A-1E) at 761, and data capture from a wearable device (e.g., a watch) at 759. The wellness tracking application can generate and maintain user profile data occurs at 757, which can include the generation and maintenance of a hand profile at 755, and can optionally also include the generation and maintenance of a writing behavior profile at 753, a stroke analysis profile at 751, and a wearable device profile at 749. The wellness tracking application can detect changes to the user profiles that exceed predetermined thresholds at 747. Optionally, a detected change can be analyzed in conjunction with a detected change in one or more other profiles to identify user wellness insights at 745. The wellness tracking application can then provide wellness insights resulting from the detection of one or more changes in the user profile that exceeded predetermined threshold levels at 743.

As discussed above, aspects of the present technology include the gathering and use of physiological information and sensor information associated with the user. In some instances, the technology may be implemented along with technologies that involve gathering personal data that relates to the user's health and/or uniquely identifies or can be used to contact or locate a specific person. In some instances, such personal data can include demographic data, date of birth, location-based data, telephone numbers, email addresses, home addresses, and data or records relating to a user's health or level of fitness (e.g., vital signs measurements, medication information, exercise information, etc.).

The present disclosure recognizes that a user's personal data, including physiological information such as data generated and used by the present technology, can be used to the benefit of users. For example, a user's input device grip pressure may allow a user to track or otherwise gain wellness insights about their health or fitness levels.

The present disclosure contemplates that the entities responsible for the collection, analysis, disclosure, transfer, storage, or other use of such personal data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should require receipt of the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. The policies and practices may be adapted depending on the geographic region and/or the particular type and nature of personal data being collected and used.

Despite the foregoing, the present disclosure also contemplates embodiments in which users selectively block the collection of, use of, or access to, personal data, including physiological information. For example, a user may be able to disable hardware and/or software elements that collect physiological or sensor information. Further, the present disclosure contemplates that hardware and/or software elements can be provided to prevent or block access to personal data that has already been collected. Specifically, users can select to remove, disable, or restrict access to certain health-related applications collecting users' personal health or fitness data.

Therefore, according to the above, some examples of the disclosure are directed to a computer-implemented method for generating wellness insights, comprising capturing first data from at least one first sensor at an input device, the captured first data including first current data captured over a first time period and first historical data captured over a second time period nonoverlapping with the first time period, generating and maintaining a user profile over the first time period and the second time period, the user profile including first profile data based at least on the first historical data, and detecting a first change between the first current data and the first profile data that exceeds a first predetermined threshold, and generating a first wellness insight based on the detected first change. Additionally or alternatively to one or more of the examples disclosed above, in some examples, the first change is detected from a comparison of the first current data with the first profile data (e.g., comparing the first current data to the first profile data). Additionally or alternatively to one or more of the examples disclosed above, in some examples the second time period precedes the first time period. Additionally or alternatively to one or more of the examples disclosed above, in some examples the capturing of the first data occurs automatically without user initiation. Additionally or alternatively to one or more of the examples disclosed above, in some examples the capturing of the first data occurs after generation of a prompt. Additionally or alternatively to one or more of the examples disclosed above, in some examples the first profile data includes an average pressure detected on a side of the input device over the second time period, and the first current data includes the average grip pressure detected on the side of the input device over the first time period. Additionally or alternatively to one or more of the examples disclosed above, in some examples the first profile data includes an average contact area computed on a side of the input device over the second time period, and the first current data includes the average contact area computed on the side of the input device over the first time period. Additionally or alternatively to one or more of the examples disclosed above, in some examples the first profile data includes an average tip pressure detected at a tip of the input device over the second time period, and the first current data includes the average tip pressure detected at the tip of the input device over the first time period. Additionally or alternatively to one or more of the examples disclosed above, in some examples the first profile data includes an average tilt angle of the input device detected over the second time period, and the first current data includes the average tilt angle of the input device detected over the first time period. Additionally or alternatively to one or more of the examples disclosed above, in some examples the first profile data includes an average temperature detected at the input device over the second time period, and the first current data includes the average temperature detected at the input device over the first time period. Additionally or alternatively to one or more of the examples disclosed above, in some examples the first profile data includes an average stability score computed over the second time period, and the first current data includes the average stability score computed over the first time period. Additionally or alternatively to one or more of the examples disclosed above, in some examples the method further comprises capturing second data from at least one second sensor at a base device, the captured second data including second current data captured over the first time period and second historical data captured over the second time period, wherein the user profile further includes second profile data based at least on the second historical data, comparing the second current data to the second profile data, and detecting a second change between the second current data and the second profile data from the comparison that exceeds a second predetermined threshold, and generating a second wellness insight based at least in part on the detected second change. Additionally or alternatively to one or more of the examples disclosed above, in some examples the second profile data includes an average pressure detected at the base device over the second time period, and the second current data includes the average pressure detected at the base device over the first time period. Additionally or alternatively to one or more of the examples disclosed above, in some examples the second profile data includes an average contact area computed at the base device over the second time period, and the second current data includes the average contact area computed at the base device over the first time period. Additionally or alternatively to one or more of the examples disclosed above, in some examples the second profile data includes an average stroke count per minute computed over the second time period, and the second current data includes the average stroke count per minute computed over the first time period. Additionally or alternatively to one or more of the examples disclosed above, in some examples the second profile data includes an average word count per minute computed over the second time period, and the second current data includes the average word count per minute computed over the first time period. Additionally or alternatively to one or more of the examples disclosed above, in some examples the second profile data includes an average time between strokes computed over the second time period, and the second current data includes the average time between strokes computed over the first time period. Additionally or alternatively to one or more of the examples disclosed above, in some examples the second profile data includes an average time between words computed over the second time period, and the second current data includes the average time between words computed over the first time period. Additionally or alternatively to one or more of the examples disclosed above, in some examples the second profile data includes an average number of corrections per minute computed over the second time period, and the second current data includes the average number of corrections per minute computed over the first time period. Additionally or alternatively to one or more of the examples disclosed above, in some examples the second profile data includes an average number of input mode switches per minute computed over the second time period, and the second current data includes the average number of input mode switches per minute computed over the first time period. Additionally or alternatively to one or more of the examples disclosed above, in some examples the second profile data includes an average number of zoom ratio switches per minute computed over the second time period, and the second current data includes the average number of zoom ratio switches per minute computed over the first time period. Additionally or alternatively to one or more of the examples disclosed above, in some examples the second profile data includes an average stroke speed computed over the second time period, and the second current data includes the average stroke speed computed over the first time period. Additionally or alternatively to one or more of the examples disclosed above, in some examples the second profile data includes an average stroke size computed over the second time period, and the second current data includes the average stroke size computed over the first time period. Additionally or alternatively to one or more of the examples disclosed above, in some examples the second profile data includes an average character recognition speed computed over the second time period, and the second current data includes the average character recognition speed computed over the first time period. Additionally or alternatively to one or more of the examples disclosed above, in some examples the second profile data includes an average character matching score determined over the second time period, and the second current data includes the average character matching score determined over the first time period. Additionally or alternatively to one or more of the examples disclosed above, in some examples the second profile data includes an average contour tracking score determined over the second time period, and the second current data includes the average contour tracking score determined over the first time period. Additionally or alternatively to one or more of the examples disclosed above, in some examples the method further comprises capturing second data from at least one second sensor at a wearable device, the captured second data including second current data captured over the first time period and second historical data captured over the second time period, wherein the user profile further includes second profile data based at least on the second historical data, comparing the second current data to the second profile data, and detecting a second change between the second current data and the second profile data from the comparison that exceeds a second predetermined threshold, and generating a second wellness insight based at least in part on the detected second change. Additionally or alternatively to one or more of the examples disclosed above, in some examples the second profile data includes an average heart rate computed over the second time period, and the second current data includes the average heart rate computed over the first time period. Some examples of the disclosure are directed to a system comprising one or more processors, memory, and one or more programs stored in the memory and configured to be executed by the one or more processors, the one or more programs including instructions for performing one or more of the example methods disclosed above. Some examples of the disclosure are directed to a non-transitory computer readable storage medium storing one or more programs, the one or more programs comprising instructions, which when executed by one or more processors of a system, cause the system to perform one or more of the example methods disclosed above. Some examples of the disclosure are directed to a system comprising one or more processors, memory, and means for performing one or more of the example methods disclosed above.

Although examples of this disclosure have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A computer-implemented method for generating wellness insights, comprising:

capturing first data from at least one first sensor at an input device, the captured first data including first current data captured over a first time period and first historical data captured over a second time period nonoverlapping with the first time period;

generating and maintaining a user profile over the first time period and the second time period, the user profile including first profile data based at least on the first historical data;

detecting a first change between the first current data and the first profile data that exceeds a first predetermined threshold; and generating a first wellness insight based on the first change.

2. The method of claim 1, wherein the capturing of the first data occurs automatically without user initiation.

3. The method of claim 1, wherein the capturing of the first data occurs after generation of a prompt.

4. The method of claim 1, wherein the first profile data includes an average pressure detected on a side of the input device over the second time period, and the first current data includes an average grip pressure detected on the side of the input device over the first time period.

5. The method of claim 1, wherein the first profile data includes an average contact area computed on a side of the input device over the second time period, and the first current data includes the average contact area computed on the side of the input device over the first time period.

6. The method of claim 1, wherein the first profile data includes an average tip pressure detected at a tip of the input device over the second time period, and the first current data includes the average tip pressure detected at the tip of the input device over the first time period.

7. The method of claim 1, wherein the first profile data includes an average tilt angle of the input device detected over the second time period, and the first current data includes the average tilt angle of the input device detected over the first time period.

8. The method of claim 1, wherein the first profile data includes an average temperature detected at the input device over the second time period, and the first current data includes the average temperature detected at the input device over the first time period.

9. The method of claim 1, wherein the first profile data includes an average stability score computed over the second time period, and the first current data includes the average stability score computed over the first time period.

10. The method of claim 1, further comprising:

capturing second data from at least one second sensor at a base device, the captured second data including second current data captured over the first time period and second historical data captured over the second time period;

wherein the user profile further includes second profile data based at least on the second historical data;

detecting a second change between the second current data and the second profile data that exceeds a second predetermined threshold; and generating a second wellness insight based at least in part on the second change.

11. The method of claim 10, wherein the second profile data includes one of an average pressure detected at the base device over the second time period or an average contact area computed at the base device over the second time period, and the second current data includes one of the average pressure detected at the base device over the first time period or the average contact area computed at the base device over the first time period.

12. The method of claim 10, wherein the second profile data includes one of an average stroke count per minute computed over the second time period, an average time between strokes computed over the second time period, an average stroke speed computed over the second time period, an average stroke size computed over the second time period, or an average contour tracking score determined over the second time period, and the second current data includes one of the average stroke count per minute computed over the first time period, the average time between strokes computed over the first time period, the average stroke speed computed over the first time period, the average stroke size computed over the first time period, or the average contour tracking score determined over the first time period.

13. The method of claim 10, wherein the second profile data includes one of an average word count per minute computed over the second time period, an average time between words computed over the second time period, an average character recognition speed computed over the second time period, or an average character matching score computed over the second time period, and the second current data includes one of the average word count per minute computed over the first time period, the average time between words computed over the first time period, the average character recognition speed computed over the first time period, or the average character matching score computed over the first time period.

14. The method of claim 10, wherein the second profile data includes an average number of corrections per minute computed over the second time period, and the second current data includes the average number of corrections per minute computed over the first time period.

15. The method of claim 10, wherein the second profile data includes an average number of input mode switches per minute computed over the second time period, and the second current data includes the average number of input mode switches per minute computed over the first time period.

16. The method of claim 10, wherein the second profile data includes an average number of zoom ratio switches per minute computed over the second time period, and the second current data includes the average number of zoom ratio switches per minute computed over the first time period.

17. The method of claim 1, further comprising:

capturing second data from at least one second sensor at a wearable device, the captured second data including second current data captured over the first time period and second historical data captured over the second time period;

wherein the user profile further includes second profile data based at least on the second historical data;

detecting a second change between the second current data and the second profile data that exceeds a second predetermined threshold; and generating a second wellness insight based at least in part on the second change.

18. The method of claim 17, wherein the second profile data includes an average heart rate computed over the second time period, and the second current data includes the average heart rate computed over the first time period.

* * * * *